United States Patent
Omran

(10) Patent No.: US 11,753,371 B2
(45) Date of Patent: Sep. 12, 2023

(54) DISULFIRAM DERIVATIVES AS ALDH1A1 AND MAGL INHIBITORS

(71) Applicant: BATTERJEE MEDICAL COLLEGE, Jeddah (SA)

(72) Inventor: Ziad Omran, Jeddah (SA)

(73) Assignee: BATTERJEE MEDICAL COLLEGE, Jeddah (SA)

( * ) Notice: Subject to any disclaimer, the term of this patent is extended or adjusted under 35 U.S.C. 154(b) by 0 days.

(21) Appl. No.: 17/540,826

(22) Filed: Dec. 2, 2021

(65) Prior Publication Data

US 2023/0174474 A1    Jun. 8, 2023

(51) Int. Cl.
  *C07C 333/26*    (2006.01)
  *C07D 409/12*    (2006.01)
  *C07D 401/12*    (2006.01)

(52) U.S. Cl.
  CPC .......... *C07C 333/26* (2013.01); *C07D 401/12* (2013.01); *C07D 409/12* (2013.01)

(58) Field of Classification Search
  CPC .... C07C 333/26; C07D 401/12; C07D 409/12
  See application file for complete search history.

(56) References Cited

U.S. PATENT DOCUMENTS

| | | | | |
|---|---|---|---|---|
| 2,784,223 A * | 3/1957 | Hosler | ........... | C07C 333/32 562/556 |
| 4,245,033 A | 1/1981 | Eida et al. | | |
| 2019/0117595 A1* | 4/2019 | Wang | ........... | A61K 31/30 |

FOREIGN PATENT DOCUMENTS

| | | | | | |
|---|---|---|---|---|---|
| CN | 106518809 A | * | 3/2017 | ........... | C07C 333/30 |
| CN | 110898049 A | * | 3/2020 | ........... | A61K 31/095 |
| CN | 111349033 A | * | 6/2020 | | |
| CN | 111378171 A | | 7/2020 | | |
| CN | 111378174 A | | 7/2020 | | |
| CN | 111378176 A | | 7/2020 | | |
| DE | 25 58 951 | | 7/1976 | | |
| EP | 0 592 283 A1 | | 4/1994 | | |

OTHER PUBLICATIONS

Yang et al. Discovery of Orally Bioavailable, Quinoline-Based Aldehyde Dehydrogenase 1A1 (ALDH1A1) Inhibitors with Potent Cellular Activity. Journal of Medicinal Chemistry 2018 61 (11), 4883-4903 (Year: 2018).*

Adeppa K, Rupainwar DC, Misra K. Development of an Improved Method for Conversion of Thiuram Disulfides into N,N-Dialkylcarbamoyl Halides and Derivatives. Synthetic Communications. 2011;41(2):285-290. doi:10.1080/00397910903537331 (Year: 2011).*

Cambridge MedChem Consulting, Bioisosteric Replacements. Retrieved from the Wayback Machine, Mar. 8, 2022, http://web.archive.org/web/20130113020012/https://www.cambridgemedchemconsulting.com/resources/bioisoteres/. Published on Jan. 13, 2013. (Year: 2013).*

McKim et al. Dimethyl Sulfoxide USP. Pharmaceutical Technology, Pharmaceutical Technology-05-02-2008, vol. 32, Issue 5. Retrieved from PharmTech, https://www.pharmtech.com/view/dimethyl-sulfoxide-usp-pheur-approved-pharmaceutical-products-and-medical-devices (Year: 2008).*

English translation of CN-111349033-A. Retrieved from Espacenet.com on Jan. 24, 2023. (Year: 2020).*

English translation of CN-110898049-A. Retrieved from Espacenet.com on Jan. 24, 2023. (Year: 2020).*

English translation of CN-106518809-A. Retrieved from Espacenet.com on Jan. 24, 2023. (Year: 2017).*

Ashenhurst, James. Tosylates and Mesylates, Master Organic Chemistry. Retrieved from the internet on Jan. 24, 2023, https://www.masterorganicchemistry.com/2015/03/10/tosylates-and-mesylates/. (Year: 2023).*

Wiggins, et al. ; Disulfiram-induced cytotoxicity and endo-lysosomal sequestration of zinc in breast cancer cells ; Biochemical Pharmacology 93 ; pp. 332-342 ; Dec. 31, 2014 ; 11 Pages.

Kapanda, et al. ; Bis(dialkylaminethiocarbonyl)disulfides as Potent and Selective Monoglyceride Lipase Inhibitors ; J. Med. Chem. 52, 22 ; pp. 7310-7314 ; Nov. 2, 2009; 10 Pages, Abstract Only.

* cited by examiner

*Primary Examiner* — Brandon J Fetterolf
*Assistant Examiner* — Lauren Wells
(74) *Attorney, Agent, or Firm* — Oblon, McClelland, Maier & Neustadt, L.L.P.

(57) ABSTRACT

A disulfiram derivative of formula (I)

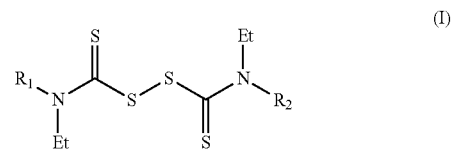

wherein $R_1$ and $R_2$ are each independently an optionally substituted alkyl, an optionally substituted cycloalkyl, an optionally substituted arylalkyl, or an optionally substituted heteroarylalkyl, and with the proviso that $R_1$ and $R_2$ are not both ethyl, both benzyl, both —$CH_2CH_2OH$, or both

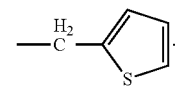

A pharmaceutical composition containing the disulfiram derivative of formula (I), and a method of treating ALDH1a1- and/or MAGL-mediated diseases or disorders.

20 Claims, No Drawings

DISULFIRAM DERIVATIVES AS ALDH1A1 AND MAGL INHIBITORS

STATEMENT OF ACKNOWLEDGEMENT

This research was supported by King Abdulaziz City for Science and Technology (KACST) under the Grant No. 2-17-03-007-0010.

STATEMENT REGARDING PRIOR DISCLOSURE BY THE INVENTORS

Aspects of this technology are described in articles titled "Development of new disulfiram analogues as ALDH1a1-selective inhibitors" published in Bioorganic & Medicinal Chemistry Letters, 40 (2021), 127958, on Mar. 17, 2021, and "New Disulfiram Derivatives as MAGL-Selective Inhibitors" published in Molecules, 2021, 26, 3296, on May 30, 2021, which are incorporated herein by reference in their entirety.

BACKGROUND OF THE INVENTION

Technical Field

The present disclosure relates to disulfiram derivatives with selective inhibitory effects on aldehyde dehydrogenase 1a1 (ALDH1a1) and/or monoacylglycerol lipase (MAGL), and methods of treating diseases associated with ALDH1a1 and MAGL using such derivatives.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The aldehyde dehydrogenases (ALDH) constitute a family of 19 enzymes involved in the metabolism of reactive aldehydes. See Jackson B, Brocker C, Thompson D C, et al. Update on the aldehyde dehydrogenase gene (ALDH) superfamily. *Hum Genomics*, 2011; 5:283. These detoxification functions impart cytoprotective roles to the ALDHs found in various tissues. See Singh S. Brocker C, Koppaka V, et al. Aldehyde dehydrogenases in cellular responses to oxidative/electrophilic stress. *Free Radic Biol Med*. 2013; 56:89-101. The ALDH enzymes also catalyze the oxidation of retinal, a limiting step during the synthesis of retinoic acid, thereby activating an important cellular differentiation pathway. Recent studies have linked ALDHs, and particularly ALDH1A1, to stem cell functions in normal as well as in cancerous tissues. See Pierre-Louis O, Clay D, Brunet de la Grange P, et al. Dual SP/ALDH functionalities refine the human hematopoietic Lin-CD34+CD38− stem/progenitor cell compartment. *Stem Cells*. 2009; 27:2552-2562; Reuben J M. Lee B-N, Gao H, et al. Primary breast cancer patients with high risk clinicopathologic features have high percentages of bone marrow epithelial cells with ALDH activity and CD44(+)CD24lo cancer stem cell phenotype. *Eur J Cancer.* 2011; 47:1527-1536; and Nwani N, Condello S, Wang Y, et al. A novel ALDH1A1 inhibitor targets cells with stem cell characteristics in ovarian cancer. Cancers (Basel). 2019; 11.

ALDH1A1 has also been identified as a distinct transcriptional regulator of metabolic responses to a high-fat diet and serves as a crucial factor in the repression of adipogenesis and diet-induced obesity. See Ziouzenkova O, Orasanu G, Sharlach M, et al. Retinaldehyde represses adipogenesis and diet-induced obesity. *Nat Med.* 2007; 13:695-702, For example, Aldh1a1$^{-/-}$ mice are resistant to diet-induced obesity and exhibit better insulin sensitivity and increased energy dissipation. Similarly, inhibition of ALDH1a1 in mice and rats reduces body weight and increases insulin sensitivity in these animals. See Ziouzenkova O, Orasanu G. Sharlach M, et al. Retinaldehyde represses adipogenesis and diet-induced obesity. *Nat Med.* 2007; 13:695-702; and Omran Z, Sheikh R, Baothman O A, Zamzami M A, Alarjah M. Repurposing Disulfiram as an anti-obesity drug: treating and preventing obesity in high-fat-fed rats. *Diabetes Metab Syndr Obes.* 2020; 13:1473-1480. The implantation of ALDH1a1-deficient adipocytes into visceral fat depots of obese large animal models, such as dogs, can also result in a markedly reduced waist circumference, lower body weight, and smaller fat mass. See Gilor C, Yang K, Lee A, et al. Thermogenic crosstalk occurs between adipocytes from different species. *Sci Rep.* 2019; 9. ALDH1a1-deficient mice are also reported to be viable and showed no growth or survival defects; thus, ALDH1a1 suppression has become an important therapeutic strategy for cancer and obesity. See Fan X, Molotkov A, Manabe S-1, et al. Targeted disruption of ALDH1a1 (Raldh1) provides evidence for a complex mechanism of retinoic acid synthesis in the developing retina. *Mol Cell Biol.* 2003; 23:4637-4648; Ciccone V, Morbidelli L, Ziche M, Donnini S. How to conjugate the sternness marker ALDH1A1 with tumor angiogenesis, progression, and drug resistance. *Cancer Drug Resistance.* 2020; 3:26-37; and Omran Z. Obesity: current treatment and future horizons. *Mini Rev Med Chem.* 2016; 17:51-61.

Disulfiram is an FDA-approved drug used to treat chronic alcoholism. This drug works by blocking the second step of ethanol metabolism by inhibiting aldehyde dehydrogenase-2 (ALDH2), the enzyme responsible for acetaldehyde oxidation into acetic acid. This leads to the accumulation of acetaldehyde in the blood following alcohol ingestion and to highly unpleasant symptoms known as acetaldehyde syndrome. Disulfiram also inhibits ALDH1a1, another member of the aldehyde dehydrogenases that catalyzes the oxidation of retinal into retinoic acid. ALDH1a1 represents a key therapeutic target for the treatment of important diseases such as cancer and obesity.

Accordingly, one aim of the present disclosure is to introduce molecules that can selectively inhibit ALDH1a1 without affecting ALDH2 activity. ALDH2 has a smaller substrate tunnel than that is present in ALDH1a1. See Moore S A, Baker H M, Blythe T J, Kitson K E, Kitson T M, Baker E N. Sheep liver cytosolic aldehyde dehydrogenase: the structure reveals the basis for the retinal specificity of class 1 aldehyde dehydrogenases. *Structure*. 1998; 6:1541-1551, incorporated herein by reference in its entirety. Therefore, the inventor envisions that designing bulkier analogues of disulfiram should allow exploitation of this difference. Since ALDH2 is involved in important physiological processes, developing selective ALDH1a1 inhibitors that do not interfere with ALDH2 would undoubtedly increase the drugability of such molecules.

Monoacylglycerol lipase (MAGL) is a serine hydrolase ~33 kDa in size that catalyzes the hydrolysis of monoglycerides (MAGs) into glycerol and free fatty acids. See Vandevoorde, S.; Saha, B.; Mahadevan, A.; Razdan, R. K.; Pertwee, R. G.; Martin, B. R.; Fowler, C. J. Influence of the degree of unsaturation of the acyl side chain upon the interaction of analogues of 1-arachidonoylglycerol with monoacylglycerol lipase and fatty acid amide hydrolase. *Biochem. Biophys. Res. Commun.* 2005, 337, 104-109. Its substrates include MAGs of different fatty acid chain lengths and degrees of saturation (e.g., 2-arachidonoyl glycerol, 2-oleylglycerol, 2-palmitoylglycerol, and 2-stearoylglycerol), but 2-arachidonoyl glycerol (2-AG) is of particular pharmacological importance because it is one of the most abundant endocannabinoids capable of activating both the CB1R and CB2R types of cannabinoid receptors. See Deng, H.; Li, W. Monoacylglycerol lipase inhibitors: Modulators for lipid metabolism in cancer malignancy, neurological and metabolic disorders. *Acta Pharm. Stn B* 2020, 10, 582-602. Thus, 2-AG has an important role in the regulation of pain sensations, addiction, neuroprotection and even food intake. See Calignano, A.; La Rana, G.; Giuffrida, A.; Piomelli, D. Control of pain initiation by endogenous cannabinoids. *Nat. Cell Biol.* 1998, 394, 277-281; Maldonado, R.; Valverde, O.; Berrendero, F. Involvement of the endocannabinoid system in drug addiction. *Trends Neurosci.* 2006, 29, 225-232; Sánchez, A.; García-Merino, A. Neuroprotective agents: Cannabinoids. *Clin. Immunol.* 2012, 142, 57-67; and Di Marzo, V.; Goparaju, S. K.; Wang, L.; Liu, J.; Bátkai, S.; Járai, Z.; Fezza. F.; Miura, G. I.; Palmiter, R. D.; Sugiura, T.; et al. Leptinregulated endocannabinoids are involved in maintaining food intake. *Nat. Cell Biol.* 2001, 410, 822-825. Conversely, arachidonic acid (AA), the main product of MAGL action on 2-AG, is a key precursor for the synthesis of proinflammatory prostaglandins. Consequently, the inhibition of MAGL will enhance endocannabinoid signaling and reduce eicosanoid production. See Nomura, D. K.; Morrison, B.; Blankman, J. L.; Long, J. Z.; Kinsey, S. G.; Marcondes, M. C. G.; Ward, A. M.; Hahn, Y. K.; Lichtman, A. H.; Conti, B.; et al. Endocannabinoid Hydrolysis Generates Brain Prostaglandins That Promote Neuroinflammation. *Science* 2011, 334, 809-813.

The endocannabinoid system is also associated with metabolic disorders. For example, Mag/–/– mice showed reductions in bodyweight and serum lipid levels compared to their wild-type counterparts. See Douglass, J. D.; Zhou, Y. X.; Wu, A.; Zadrogra, J. A.; Gajda, A. M.; Lackey, A. I.; Lang, W.; Chevalier, K. M.; Sutton, S. W.; Zhang, S.-P.; et al. Global deletion of MGL in mice delays lipid absorption and alters energy homeostasis and diet-induced obesity. *J. Lipid Res.* 2015, 56, 1153-1171. MAGL inhibitors also prevented glucose-stimulated and depolarization-induced insulin secretion. See Berdan, C. A.; Erion, K. A.; Burritt, N. E.; Corkey, B. E.; Deeney, J. T. Inhibition of Monoacylglycerol Lipase Activity Decreases Glucose-Stimulated Insulin Secretion in INS-1 (832/13) Cells and Rat Islets. *PLoS ONE* 2016, 11, e0149008. Therefore, MAGL inhibition also represents a plausible strategy for the treatment of metabolic disorders. See Deng, H.; Li, W. Monoacylglycerol lipase inhibitors: Modulators for lipid metabolism in cancer malignancy, neurological and metabolic disorders. *Acta Pharm. Sin. B* 2020, 10, 582-602.

MAGL also plays a pathophysiological role in aggressive cancers, showing overexpression in aggressive human cancer cells and primary tumors ranging from prostate cancer to colorectal cancer, hepatocellular carcinoma and nasopharyngeal carcinoma. See Nomura, D. K.; Long, J. Z.; Niessen, S.; Hoover. H. S.; Ng, S.-W.; Cravatt, B. F. Monoacylglycerol Lipase Regulates a Fatty Acid Network that Promotes Cancer Pathogenesis. *Cell* 2010, 140, 49-61; Nomura, D. K.; Lombardi, D. P.; Chang, J. W.; Niessen, S.; Ward, A. M.; Long, J. Z.; Hoover. H. H.; Cravatt, B. F. Monoacylglycerol Lipase Exerts Dual Control over Endocannabinoid and Fatty Acid Pathways to Support Prostate Cancer. *Chem. Biol.* 2011, 18, 846-856; Ye, L.; Zhang, B.; Seviour, E.; Tao, K.-X.; Liu, X.-H.; Ling, Y.; Chen, J.-Y.; Wang, G.-B. Monoacylglycerol lipase (MAGL) knockdown inhibits tumor cells growth in colorectal cancer. *Cancer Lett.* 2011, 307, 6-17; and Zhang, J.; Liu, Z.; Lian, Z.; Liao, R.; Chen, Y.; Qin, Y.; Wang, J.; Jiang, Q.; Wang, X.; Gong, J. Monoacylglycerol Lipase: A Novel Potential Therapeutic Target and Prognostic Indicator for Hepatocellular Carcinoma. *Sci. Rep.* 2016, 6, 35784. It is believed that MAGL functions through its regulation of an oncogenic signaling network of lipids by supplying a pool of free fatty acids (FFAs) that promote the migration, invasion and survival of cancer cells. Consequently, reducing the FFA levels by inhibiting MAGL also decreases cancer aggressiveness, independently of endocannabinoid signaling. These reductions in FFA levels by MGAL inhibition are only observed in aggressive cancers, because in healthy tissues MAGL controls the MAG levels but not the FFA levels. The levels of known oncogenic lysophospholipids, such as phosphatidic acid and prostaglandin (PGE2), are also significantly reduced if MAGL is inhibited. As an added benefit, MAGL inhibition also has a positive impact on cancer-associated symptoms, including pain and nausea. See Sticht, M.; Long, J. Z.; Rock, E. M.; Limebeer, C. L.; Mechoulam, R.; Cravatt, B. F.; Parker. L. Inhibition of monoacylglycerol lipase attenuates vomiting in Suncus murinus and 2-arachidonoyl glycerol attenuates nausea in rats. *Br. J. Pharmacol.* 2012, 165, 2425-2435. Also, MAGL is the main enzyme responsible for 2-AG in catabolism in the brain. See Blankman, J. L.; Simon, G. M.; Cravatt, B. F. A Comprehensive Profile of Brain Enzymes that Hydrolyze the Endocannabinoid 2-Arachidonoylglycerol. *Chem. Biol.* 2007, 14, 1347-1356; and Muccioli, G.; Xu, C.; Odah, E.; Cudaback, E.; Cisneros, J. A.; Lambert, D. M.; Lopez-Rodriguez, M. L.; Bajalieh, S.; Stella, N. Identification of a Novel Endocannabinoid-Hydrolyzing Enzyme Expressed by Microglial Cells. *J. Neurosci.* 2007, 27, 2883-2889.

Accordingly, MAGL inhibition may serve as a new therapeutic avenue for the treatment of inflammation, neurodegeneration, metabolic disorders and cancers. In fact, a MAGL inhibitor, ABX-1431, is currently undergoing phase-II clinical trials to test its efficacy in treating two neurological disorders, namely Tourette syndrome and motor tic disorder. See Deng, H.; Li, W. Monoacylglycerol lipase inhibitors: Modulators for lipid metabolism in cancer malignancy, neurological and metabolic disorders. *Acta Pharm. Sin. B* 2020, 10, 582-602. Despite these recent efforts, there is still a need to develop effective disulfiram analogues that can selectively inhibit MAGL activity.

In view of the forgoing, one objective of the present disclosure is to provide potent and selective therapeutic disulfiram derivatives with low- and sub-micromolar inhibitory activities against ALDH1a1 and/or MAGL, a pharmaceutical composition containing the disulfiram derivatives, and a method for treating diseases or disorders associated with ALDH1a1 and MAGL.

BRIEF SUMMARY OF THE INVENTION

According to a first aspect, the present disclosure relates to a disulfiram derivative of formula (I),

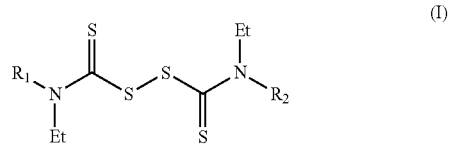

or a salt thereof, a solvate thereof, a tautomer thereof, a stereoisomer thereof, or a mixture thereof, wherein (i) $R_1$ and $R_2$ are each independently selected from the group consisting of an optionally substituted alkyl, an optionally substituted cycloalkyl, an optionally substituted arylalkyl, and an optionally substituted heteroarylalkyl, and (ii) with the proviso that $R_1$ and $R_2$ are not both ethyl, both benzyl, both —CH$_2$CH$_2$OH, or both

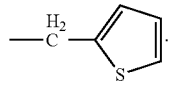

In one embodiment, $R_1$ and $R_2$ are each independently a $C_1$ to $C_6$ alkyl, a $C_7$ to $C_{12}$ arylalkyl, or a $C_5$ to $C_{10}$ heteroarylalkyl.

In one embodiment, $R_1$ and $R_2$ are each independently selected from the group consisting of —CH$_2$CH$_2$COOH, —CH$_2$CH$_2$COOEt,

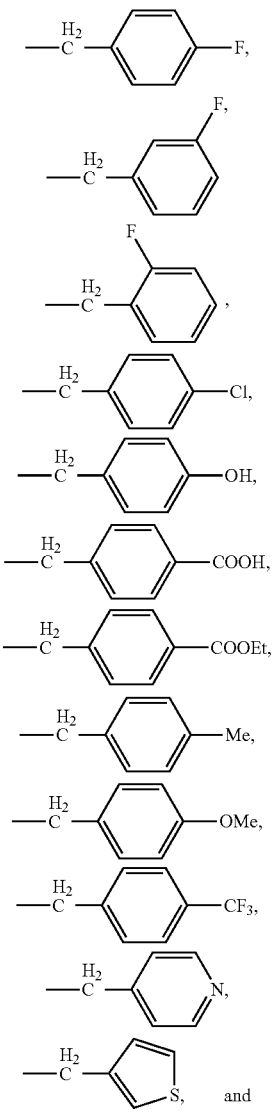

-continued

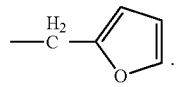

In one embodiment, $R_1$ and $R_2$ are the same.

In one embodiment, the disulfiram derivative of formula (I) is selected from the group consisting of

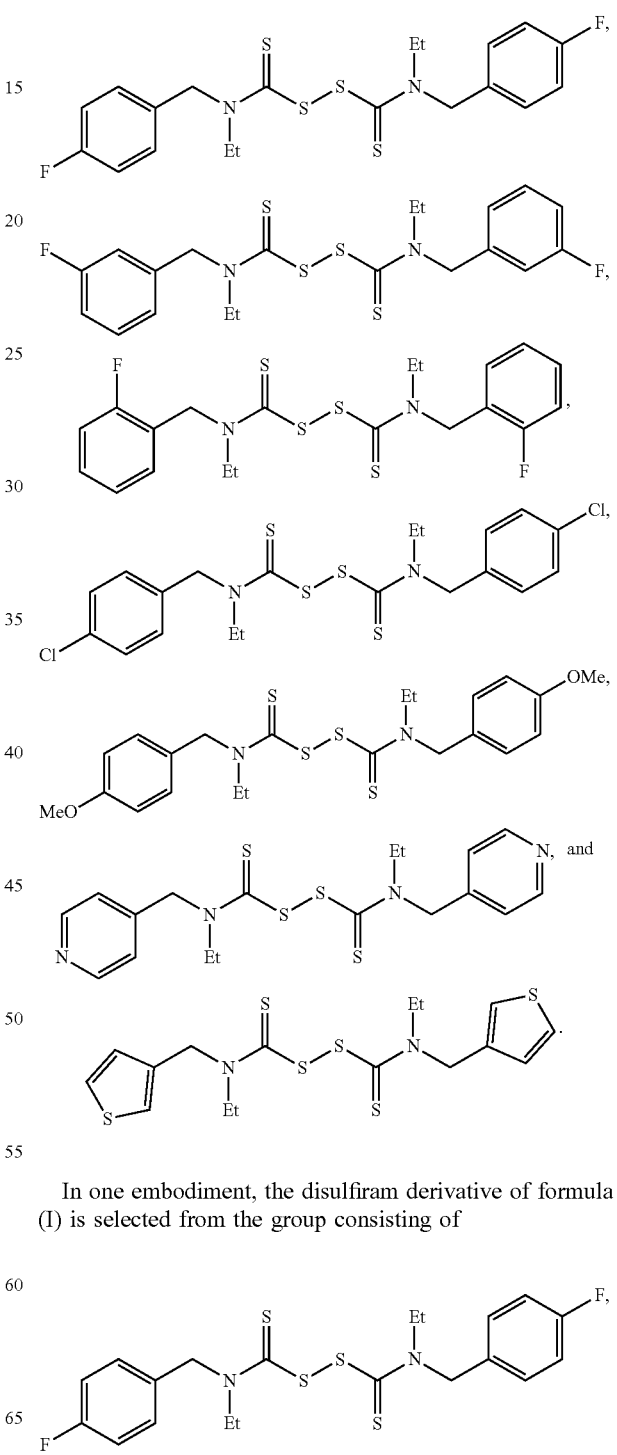

In one embodiment, the disulfiram derivative of formula (I) is selected from the group consisting of

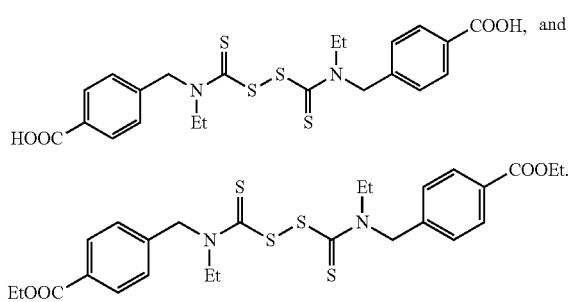

In a further embodiment, the disulfiram derivative of formula (I) is devoid of inhibitory effect on aldehyde dehydrogenase 2 (ALDH2).

In one embodiment, the disulfiram derivative of formula (I) is

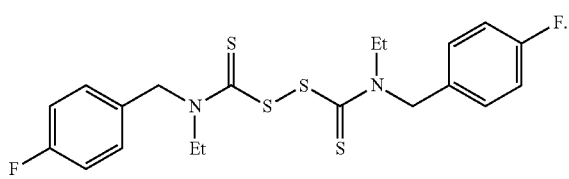 [SMILES: CCN(Cc1ccc(F)cc1)C(=S)SSC(=S)N(CC)Cc1ccc(F)cc1]

In one embodiment, the disulfiram derivative of formula (I) is devoid of inhibitory effect on fatty acid amide hydrolase (FAAH).

In one embodiment, the disulfiram derivative of formula (I) has an $IC_{50}$ for aldehyde dehydrogenase 1a1 (ALDH1a1) of 0.1-10 μM.

In one embodiment, the disulfiram derivative of formula (I) has an $IC_{50}$ for monoacylglycerol lipase (MAGL) of 0.5-50 μM.

According to a second aspect, the present disclosure relates to a pharmaceutical composition containing the disulfiram derivative of formula (I) of the first aspect and a pharmaceutically acceptable carrier and/or excipient.

In one embodiment, the disulfiram derivative of formula (I) is present in the pharmaceutical composition in a concentration of 1 to 50 μM, relative to a total volume of the pharmaceutical composition.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

According to a third aspect, the present disclosure relates to a method of treating an ALDH1a1 mediated disease or disorder in a subject. The method involves administering to the subject a therapeutically effective amount of the disulfiram derivative of formula (I) of the first aspect.

In one embodiment, the therapeutically effective amount of the disulfiram derivative of formula (I) is from 0.01 to 50 mg/kg of the disulfiram derivative of formula (I) per body weight of the subject.

In one embodiment, the disulfiram derivative of formula (I) is selected from the group consisting of

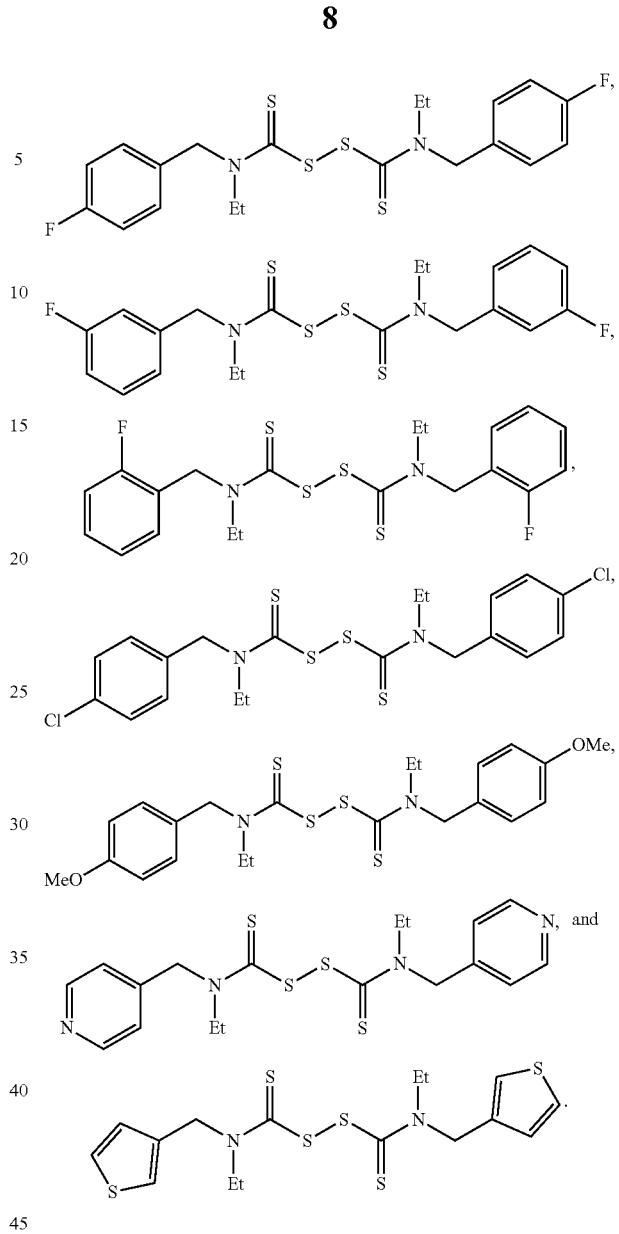

According to a fourth aspect, the present disclosure relates to a method of treating a MAGL-mediated disease or disorder in a subject. The method involves administering to the subject a therapeutically effective amount of the disulfiram derivative of formula (I) of the first aspect.

In one embodiment, the therapeutically effective amount of the disulfiram derivative of formula (I) is from 0.01 to 50 mg/kg of the disulfiram derivative of formula (I) per body weight of the subject.

In one embodiment, the disulfiram derivative of formula (I) is selected from the group consisting of

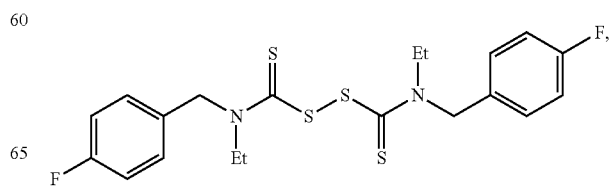

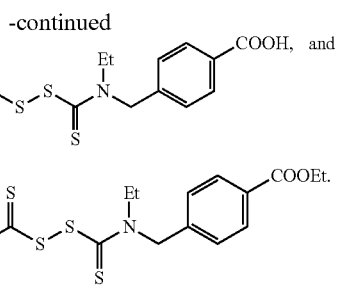

The foregoing paragraphs have been provided by way of general introduction, and are not intended to limit the scope of the following claims. The described embodiments, together with further advantages, will be best understood by reference to the following detailed description taken in conjunction with the accompanying drawings.

DETAILED DESCRIPTION OF THE EMBODIMENTS

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "derivative," "analogue," "compound," and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, iso-propanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (TIF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomers refer to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, cycloheptyl, cyclooctyl, norbornyl, and adamantyl. Branched cycloalkyl groups such as exemplary 1-methylcyclopropyl and 2-methylcyclopropyl groups and cycloalkenyl groups such as cyclobutenyl, cyclopentenyl, and cyclohexenyl are included in the definition of cycloalkyl as used in the present disclosure.

The term "aryl", as used herein, and unless otherwise specified, refers to a substituent that is derived from an aromatic hydrocarbon (arene) that has had a hydrogen atom removed from a ring carbon atom. The aryl group may be a carbocyclic aromatic monocyclic group containing 6 carbon atoms which may be further fused to one or more 5- or 6-membered carbocyclic group which may be aromatic, saturated or unsaturated. Aryl includes, but is not limited to, phenyl, biphenyl, 1-naphthyl, 2-naphthyl, anthracenyl, and the like.

The term "heteroaryl" is intended to mean stable monocyclic and polycyclic aromatic hydrocarbons that include at least one heteroatom ring member such as sulfur, oxygen, or nitrogen. Heteroaryl groups are heterocyclyl groups which are aromatic, and may include, without limitation, pyridyl, pyrrolyl, pyrimidinyl, pyrazinyl, pyridazinyl, triazinyl, furyl, quinolyl, isoquinolyl, thienyl, imidazolyl, thiazolyl, indolyl (e.g., 1H-indolyl), pyrroyl, oxazolyl, benzofuryl, benzothienyl, benzthiazolyl, isoxazolyl, pyrazolyl, triazolyl, tetrazolyl, indazolyl (e.g., 1H-indazolyl), 1,2,4-thiadiazolyl, isothiazolyl, purinyl, carbazolyl, benzimidazolyl, indolinyl, benzodioxolanyl, and benzodioxane. Heteroaryl groups may be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→0 and S(O)$_p$, wherein p is 0, 1 or 2).

The term "arylalkyl", as used herein, refers to a straight or branched chain alkyl moiety (as defined above) that is substituted by an aryl group (as defined above), and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "heteroarylalkyl", as used herein, refers to a straight or branched chain alkyl moiety (as defined above) that is substituted by an heteroaryl group as hereinbefore defined via carbon atom(s) or heteroatom(s). Examples of heteroarylalkyl include, without limitation, imidazol-2-ylmethyl, 2-pyridinylmethyl, 4-pyridinylmethyl, 2-thienylmethyl, 3-thienylmethyl, 2-furylmethyl, 3-furylmethyl, and the like.

The term "halogen", as used herein, means fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, arnlkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}$C and $^{14}$C, isotopes of nitrogen include $^{14}$N and $^{15}$N, and isotopes of oxygen include $^{16}$O, $^{17}$O and $^{18}$O. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

Drugs that can inhibit aldehyde dehydrogenase (ALDH) activities include disulfiram, an FDA-approved drug for the treatment of chronic alcoholism. This drug blocks ethanol metabolism at the aldehyde stage, leading to the accumulation of acetaldehyde in the blood. The result is a series of highly unpleasant reactions, including hypotension, tachycardia, tachypnoea, vomiting, and vertigo when a patient treated with disulfiram consumes even small amounts of alcohol. See Bell R G, Smith H W. Preliminary report on clinical trials of antabuse. *Can Med Assoc J.* 1949; 60:286-288, incorporated herein by reference in its entirety. Disulfiram is metabolized in-vivo into many thiol-reacting species such as S-methyl-N, N-diethylthiocarbamate, S-methyl-N, N-diethyldithiocarbamate and their sulfoxides and sulfones. See Koppaka V, Thompson D C, Chen Y, et al. Aldehyde dehydrogenase inhibitors: a comprehensive review of the pharmacology, mechanism of action, substrate specificity, and clinical application. *Pharmacol Rev.* 2012; 64:520-539; and Lipsky J J, Shen M L, Naylor S. In vivo inhibition of aldehyde dehydrogenase by disulfiram. (*Chem Biol Interact.* 2001; 130-132:93-102, each incorporated herein by reference in their entirety. These metabolites are responsible for the irreversible inhibition of ALDHs by disulfiram by carbamylation of the catalytic Cys302 residue. Many studies have now indicated the potential of repurposing disulfiram as an anticancer agent, and disulfiram is currently undergoing several clinical trials to treat different types of cancers, including metastatic breast cancer, glioblastoma, and recurrent pancreatic carcinoma. See Lipsky J J, Shen M L, Naylor S. In vivo inhibition of aldehyde dehydrogenase by disulfiram. *Chem Biol Interact.* 2001; 13(1-32:93-102; and Yang Q, Yao Y. Li K, et al. An updated review of disulfiram: molecular targets and strategies for cancer treatment. *Curr Pharm Des.* 2019; 25:3248-3256, each incorporated herein by reference in their entirety.

Disulfiram, which has been approved by the FDA as an aldehyde dehydrogenase inhibitor for the treatment of chronic alcoholism, is another drug that can inhibit MAGL activity. See LaBar, G.; Bauvois, C.; Muccioli, G. G.; Wouters, J.; Lambert, D. M. Disulfiram is an Inhibitor of Human Purified Monoacylglycerol Lipase, the Enzyme Regulating 2-Arachidonoylglycerol Signaling. *ChemBioChem* 2007, 8, 1293-1297, incorporated herein by reference in its entirety. Disulfiram was shown to irreversibly inhibit MAGL by the carbamylation of Cys208 and Cys242, which are located in the vicinity of the MAGL active site. See Kapanda, C. N.; Muccioli, G. G.; LaBar, G.; Poupaert, J. H.; Lambert, D. M. Bis(dialkylaminethiocarbonyl)disulfides as Potent and Selective Monoglyceride Lipase Inhibitors. *J. Med. Chem.* 2009, 52, 7310-7314; and Saario, S. M.; Salo-Ahen, O. M. H.; Nevalainen, T.; Poso, A.; Laitinen, J. T.; Järvinen, T.; Niemi, R. Characterization of the Sulfhydryl-Sensitive Site in the Enzyme Responsible for Hydrolysis of 2-Arachidonoyl-Glycerol in Rat Cerebellar Membranes. *Chem. Biol.* 2005, 12, 649-656, each incorporated herein by reference in their entirety. In addition to its inhibition of MAGL, disulfiram inhibits fatty acid amide hydrolase (FAAH), an enzyme responsible for the hydrolysis of both 2-AG and N-arachidonoylethanolamine. See Kapanda, C. N.; Muccioli, G. G.; LaBar, G.; Poupaert, J. H.; Lambert, D. M. Bis(dialkylaminethiocarbonyl)disulfides as Potent and Selective Monoglyceride Lipase Inhibitors. *J. Med. Chem.* 2009, 52, 7310-7314; and Cravatt, B. F.; Giang, D. K.; Mayfield, S. P.; Boger, D. L.; Lerner, R. A.; Gilula, N. B. Molecular characterization of an enzyme that degrades neuromodulatory fatty-acid amides. *Nat. Cell Biol.* 1996, 384, 83-87, each incorporated herein by reference in their entirety.

The present disclosure provides disulfiram derivatives (i.e., analogues) having medicinal or pharmaceutical properties, preferably inhibitory activities against aldehyde dehydrogenase 1a1 (ALDH1a1) and/or monoacylglycerol lipase (MAGL) with high selectivity. The chemical structure of disulfiram is shown below:

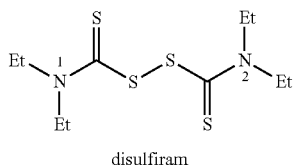

disulfiram

In the presently disclosed disulfiram derivatives, at least one ethyl group of the disulfiram structure, preferably one ethyl group bonded to each of the two nitrogen atoms (N1 and N2), is replaced with an alkyl group other than ethyl, or a cycloalkyl, an arylalkyl, or a heteroarylalkyl.

According to a first aspect, the present disclosure relates to a disulfiram derivative of formula (I),

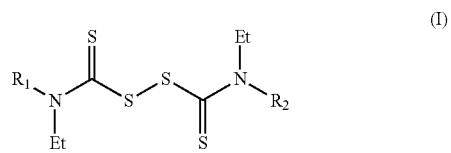

or a salt thereof, a solvate thereof, a tautomer thereof, a stereoisomer thereof, or a mixture thereof, wherein: $R_1$ and $R_2$ are each independently selected from the group consisting of an optionally substituted alkyl, an optionally substituted cycloalkyl, an optionally substituted arylalkyl, and an optionally substituted heteroarylalkyl, and with the proviso that $R_1$ and $R_2$ are not both ethyl, both benzyl, both —$CH_2CH_2OH$, or both

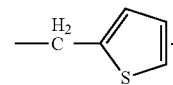

In terms of $R_1$ and $R_2$, these substituents may be the same or different. Preferably $R_1$ and $R_2$ are the same.

In one embodiment, $R_1$ and $R_2$ are each independently an optionally substituted alkyl. In a preferred embodiment, $R_1$ and $R_2$ are each independently an optionally substituted $C_{1-6}$ alkyl, preferably an optionally substituted $C_{2-5}$ alkyl, preferably an optionally substituted $C_{3-4}$ alkyl. The carbon counts described herein refers to a number of carbon atoms of the alkyl group of $R_1$ or $R_2$ which excludes the carbon atoms of optionally present substituents. The alkyl may be linear or branched. Exemplary linear alkyls include, but are not limited to methyl, ethyl, n-propyl, n-butyl, n-pentyl, n-hexyl, n-heptyl, and n-octyl. Non-limiting examples of branched alkyls include isopropyl, sec-butyl, isobutyl, isobutyl, tert-butyl, isopentyl, neopentyl, and isohexyl. In at least one embodiment, $R_1$ and $R_2$ are not both ethyl.

Preferably, the alkyl of $R_1$ or $R_2$ is substituted with at least one substituent such as a hydroxy, a carboxy, an alkoxy (e.g. methoxy, ethoxy), an ester (e.g., methyl ester, ethyl ester), and a halogen group (e.g. chloro, fluoro). In most preferred embodiments, $R_1$ and $R_2$ are alkyl selected from —$CH_2CH_2COOH$, and —$CH_2CH_2COOEt$. In at least one embodiment, $R_1$ and $R_2$ are not both —$CH_2CH_2OH$.

In another embodiment, $R_1$ and $R_2$ are each independently an optionally substituted arylalkyl. As defined above, an "arylalkyl" group refers to an aryl group which is linked to a base molecule through an alkylene linker. The arylalkyl groups are described by the total number of carbon atoms in the aryl ring and linker. Thus, a benzyl group is a $C_7$-arylalkyl group and a phenylethyl is a $C_8$-arylalkyl. The arylalkyl groups disclosed herein may contain 7-16 carbon atoms ("$C_7$-$C_{16}$ arylalkyl"), wherein the aryl portion contains 6-12 carbon atoms, and the alkylene linker contains 1-4 carbon atoms.

In a preferred embodiment, $R_1$ and $R_2$ are each independently an optionally substituted $C_7$ to $C_{12}$ arylalkyl, preferably an optionally substituted $C_8$ to $C_{11}$ arylalkyl, preferably an optionally substituted $C_9$ to $C_{10}$ arylalkyl. The carbon counts described herein refers to a number of carbon atoms of the arylalkyl group of $R_1$ or $R_2$ which excludes the carbon atoms of optionally present substituents.

Preferably, the arylalkyl of $R_1$ or $R_2$ is a benzyl group having at least one hydrogen of the aromatic ring (i.e., phenyl) substituted with group(s) such as a halogen (e.g., fluoro, chloro, bromo, iodo), a hydroxy, a carboxy, an ester (e.g., methyl ester, ethyl ester), an alkoxy (e.g. methoxy, ethoxy), an alkyl (e.g., methyl, trifluoromethyl, ethyl), an amino (e.g. dimethylamino), nitro, and cyano. The substitution may occur on the para-, meta-, and/or ortho-position, preferably on para-position on phenyl ring of the benzyl group. In preferred embodiments, $R_1$ and $R_2$ are arylalkyl selected from

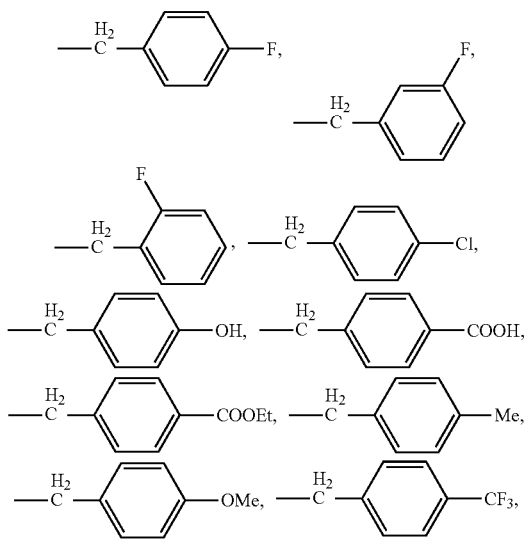

most preferably

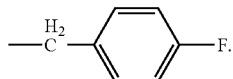

In a at least one embodiment, $R_1$ and $R_2$ are not both benzyl.

In another embodiment, $R_1$ and $R_2$ are each independently an optionally substituted heteroarylalkyl. As described above, a "heteroarylalkyl" refers to a heteroaryl group that is attached to a base molecule via an alkylene linker. Unsubstituted heteroarylalkyl groups disclosed herein may contain 6-20 non-hydrogen atoms (including C, N, S and O atoms), wherein the heteroaryl portion contains 5-12 atoms and the alkylene portion contains 1-4 carbon atoms.

In a preferred embodiment, $R_1$ and $R_2$ are each independently an optionally substituted $C_5$ to $C_{10}$ heteroarylalkyl, preferably an optionally substituted $C_6$ to $C_9$ heteroarylalkyl, preferably an optionally substituted $C_7$ to $C_8$ heteroarylalkyl. The carbon counts described herein refers to a number of carbon atoms of the heteroarylalkyl group of $R_1$ or $R_2$ which excludes the carbon atoms of optionally present substituents.

Preferably, the heteroarylalkyl of $R_1$ or $R_2$ is unsubstituted. Exemplary unsubstituted heteroarylalkyls include, but are not limited to, 4-pyridylmethyl

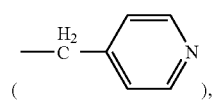

2-pyridylmethyl, 2-thienylmethyl

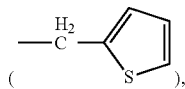

3-thienylmethyl

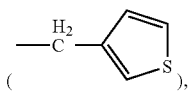

2-furylmethyl

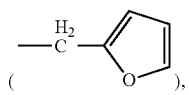

3-furylmethyl, 2-benzimidazolylmethyl, 2-furylethyl, pyrimidinylmethyl, tetrazol-5-ylmeth 1, and the like. In preferred embodiments, $R_1$ and $R_2$ are heteroarylalkyl selected from

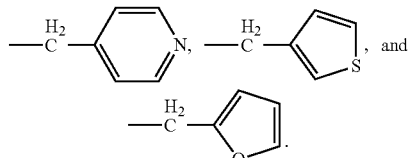

In at least one embodiment, $R_1$ and $R_2$ are not both

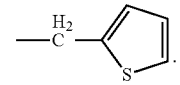

In preferred embodiments, the disulfiram derivative of formula (I) is selected from the group consisting of

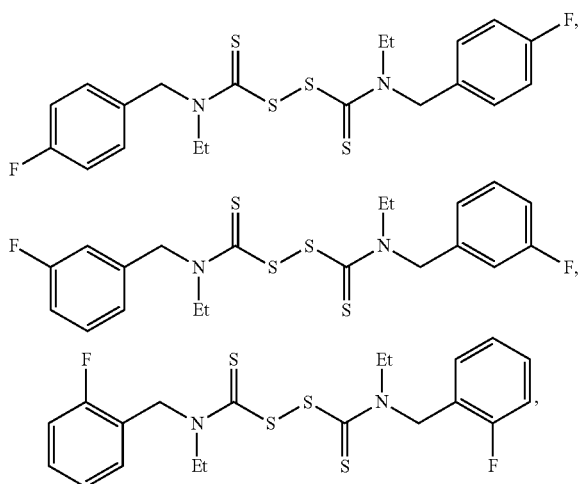

-continued

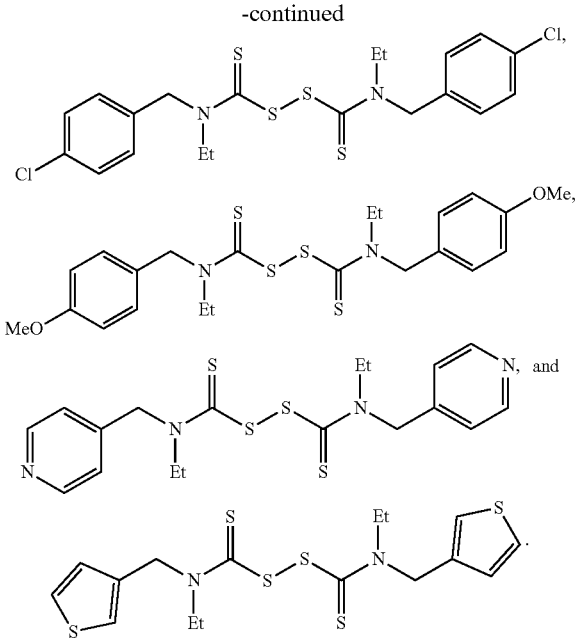

In preferred embodiments, the disulfiram derivative of formula (I) is selected from the group consisting of

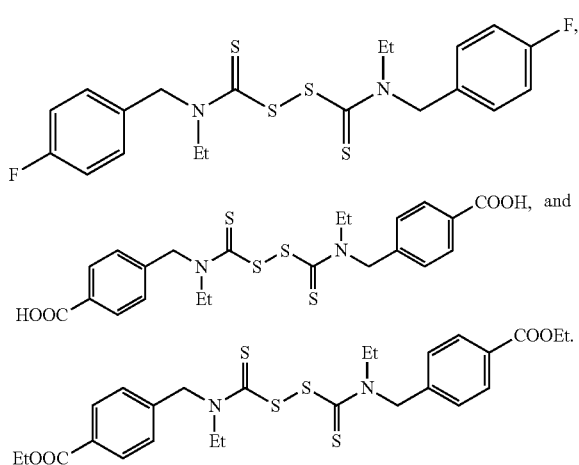

In the most preferred embodiments, the disulfiram derivative of formula (I) is

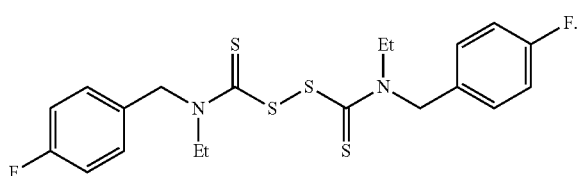

The disulfiram derivatives of formula (I) are capable of inhibiting the action of aldehyde dehydrogenase 1a1 (ALDH1a1) and/or monoacylglycerol lipase (MAGL). The inhibitory activity of the disulfiram derivatives may be expressed as half maximal inhibitory concentration ($IC_{50}$) values. As is well understood in the art, the $IC_{50}$ value of a compound/composition is a concentration of that compound/composition needed to inhibit, in vitro, a certain biological process or component (e.g., an enzyme) by 50%. Typically, a higher value of $IC_{50}$ indicates a greater inhibitory activity.

In some embodiments, the $IC_{50}$ of the presently disclosed disulfiram derivatives of formula (I), the salt thereof, the solvate thereof, the tautomer thereof, the stereoisomer thereof, or mixtures thereof against ALDH1a1 is less than 100 μM, preferably less than 75 μM, preferably less than 50 μM, preferably less than 30 μM, preferably less than 10 μM, preferably less than 5 μM, preferably less than 2 μM, preferably less than 1 μM. In at least one embodiment, the $IC_{50}$ of the of the disulfiram derivatives of formula (I), the salt thereof, the solvate thereof, the tautomer thereof, the stereoisomer thereof, or mixtures thereof against ALDH1a1 is from 0.01 to 25 μM, preferably from 0.02 to 20 μM, preferably from 0.05 to 15 μM, preferably from 0.1 to 10 μM, preferably from 0.15 to 5 μM, preferably from 0.17 to 2.5 μM, preferably from 0.2 to 2 μM, preferably from 0.3 to 1.5 μM, preferably from 0.4 to 1.25 μM, preferably from 0.5 to 1 μM, preferably from 0.6 to 0.9 μM, preferably from 0.7 to 0.8 μM.

In some embodiments, the $IC_{50}$ of the presently disclosed disulfiram derivatives of formula (I), the salt thereof, the solvate thereof, the tautomer thereof, the stereoisomer thereof, or mixtures thereof against MAGL is less than 100 μM, preferably less than 75 μM, preferably less than 50 μM, preferably less than 30 μM, preferably less than 10 μM, preferably less than 5 μM, preferably less than 2 μM, preferably less than 1 μM. In at least one embodiment, the $IC_{50}$ of the of the disulfiram derivatives of formula (I), the salt thereof, the solvate thereof, the tautomer thereof, the stereoisomer thereof, or mixtures thereof against MAGL is from 0.1 to 75 μM, preferably from 0.5 to 50 μM, preferably from 1 to 30 μM, preferably from 2 to 25 μM, preferably from 3 to 20 μM, preferably from 4 to 18 μM, preferably from 5 to 15 μM, preferably from 6 to 12 μM, preferably from 7 to 10 μM, preferably from 8 to 9 μM.

Notably, the disulfiram derivatives disclosed herein inhibit ALDH1a1 and MAGL enzymes with high selectivity. For example, within the family of ALDH enzymes, $IC_{50}$ of the disulfiram derivatives of formula (I) against aldehyde dehydrogenase 2 (ALDH2) is at least 5 times greater than that against ALDH1a1, preferably at least 10 times greater, preferably at least 25 times greater, preferably at least 50 times greater, preferably at least 100 times greater, preferably at least 200 times greater, preferably at least 250 times greater, preferably at least 500 times greater, preferably at least 1,000 times greater than that against ALDH1a1 (see e.g., Tables I and III of the Examples). In at least one embodiment, when the disulfiram derivative of formula (I) is selected from the group consisting of

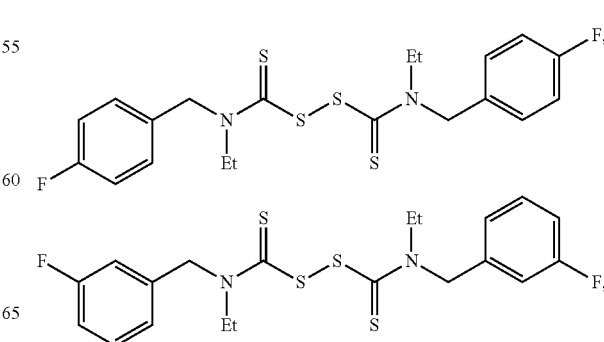

-continued

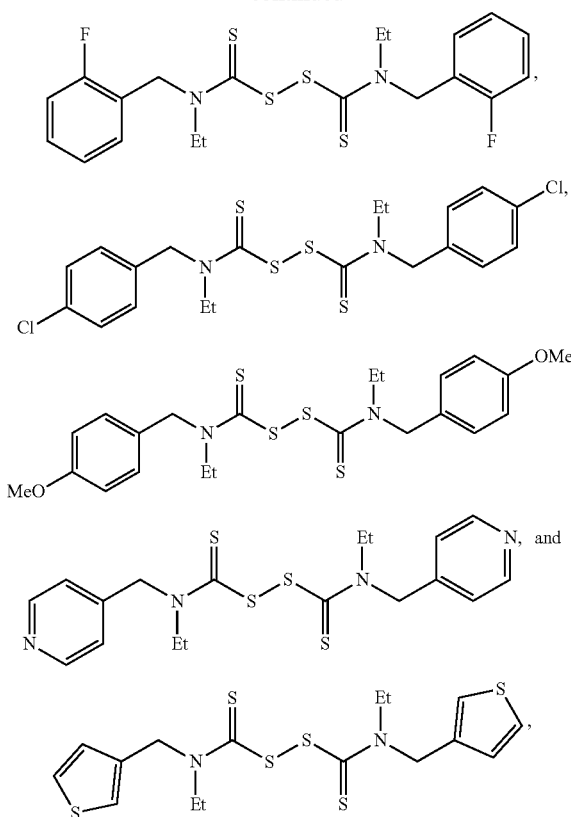

the derivative is devoid of inhibitory activity on ALDH2. Such improved selectivity of the disulfiram derivatives can reduce or prevent adverse side effects, including impairment of the central nervous system (e.g., seizures).

Alternatively, the disulfiram derivative of formula (I) exhibits dual ALDH1a1/ALDH2 inhibition if it is selected from the group consisting of

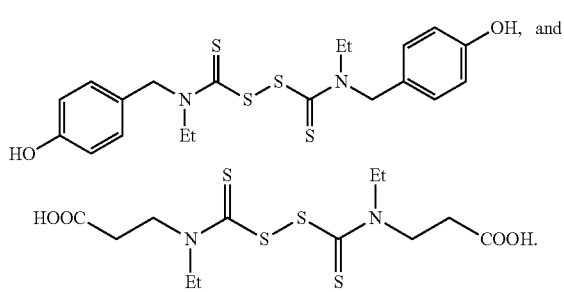

Additionally, $IC_{50}$ of the disulfiram derivatives of formula (I) against fatty acid amide hydrolase (FAAH) is at least 3 times greater than that against MAGL, preferably at least 4 times greater, preferably at least 5 times greater, preferably at least 8 times greater, preferably at least 10 times greater, preferably at least 15 times greater, preferably at least 25 times greater, preferably at least 35 times greater, preferably at least 50 times greater than that against MAGL (see e.g., Table II of the Examples). In at least one embodiment, when the disulfiram derivative of formula (I) is selected from the group consisting of

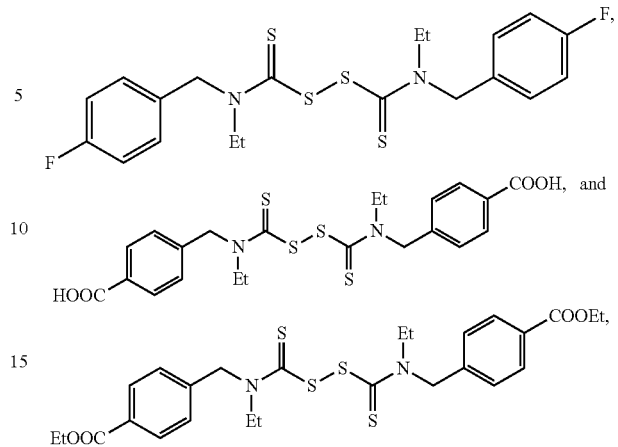

the derivative is devoid of inhibitory activity on FAAH.

Alternatively, the disulfiram derivative of formula (I) exhibits dual MAGL/FAAH inhibition if it is selected from the group consisting of

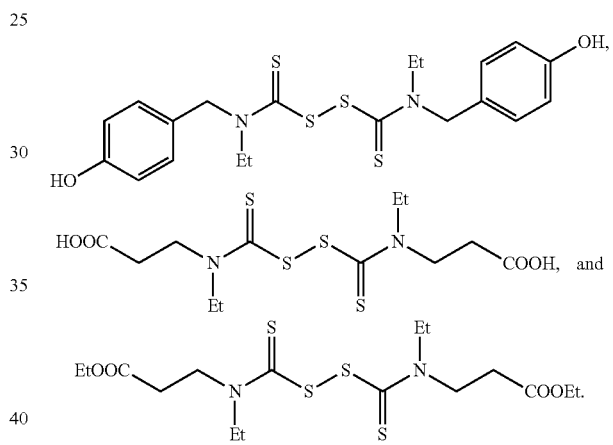

The disulfiram derivatives of the present disclosure may be prepared by any synthesis method know to those of ordinary skill in the art. The following methods set forth below are provided for illustrative purposes and not intended to limit the scope of the disclosure.

The disulfiram derivatives may, for example, be synthesized by mixing a first amine of formula (II)

or a salt, solvate, tautomer or stereoisomer thereof, a second amine of formula (III)

or a salt, solvate, tautomer or stereoisomer thereof, and carbon disulfide (CS$_2$) in the presence of an oxidizing agent, wherein R$_1$ and R$_2$ are as previously specified. Preferably, R$_1$ and R$_2$ are the same, and a single amine is used herein as the first and second amines. In particular, the disulfiram derivatives may be synthesized according to route (i) or (ii) illustrated in Table A/B, below.

Exemplary oxidizing agents include, but are not limited to, carbon tetrabromide (CBr$_4$), sodium nitrite (NaNO$_2$), hydrogen peroxide (H$_2$O$_2$), sodium hypochlorite (NaClO), chlorine (Cl$_2$), and iodine (I$_2$). In preferred embodiments, oxidizing agent used herein is carbon tetrabromide or sodium nitrite.

The reaction forming the disulfiram derivatives of formula (I) may be performed by mixing the amines and CS$_2$ preferably in a solvent or in neat condition (i.e., solvent free) to form a reaction mixture. Exemplary solvent useful for the reaction include organic solvents or water. Non-limiting examples of organic solvent include, but are not limited to, aromatic solvents (e.g., benzene, ethylbenzene, o-xylene, m-xylene, p-xylene, and mixtures of xylenes, toluene, mesitylene, anisole, 1,2-dimethoxybenzene, α,α,α,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof.

When the R$_1$ and R$_2$ groups of disulfiram derivatives have mild polarity

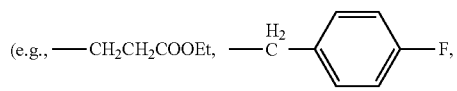

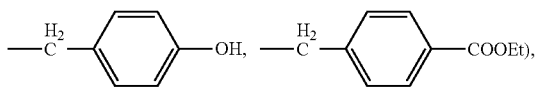

the solvent is preferably one or more organic solvents, most preferably dimethyl formamide (DMF). In a related embodiment, when an organic solvent (e.g., DMF) is used, the oxidizing agent is preferably carbon tetrabromide. Alternatively, when the R$_1$ and R$_2$ groups of disulfiram derivatives have large polarity

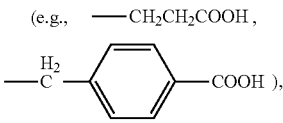

the solvent is preferably water, or an aqueous solution. In a related embodiment, when water is used as the solvent, the oxidizing agent is preferably sodium nitrite.

Typically, the amine starting material (e.g., the first and second amines of formulae (II) and (III)), is present in the reaction mixture at a concentration in a range of 0.01-20 M, preferably 0.05-15 M, preferably 0.1-10 M, preferably 0.5-5 M, preferably 1-2 M. In a related embodiment, CS$_2$ is present in the reaction mixture at a concentration in a range of 0.005-10 M, preferably 0.075-7.5 M, preferably 0.1-5 M, preferably 0.2-2 M, preferably 0.4-1 M, preferably 0.5-0.8 M. In another related embodiment, the oxidizing agent is present in the reaction mixture at a concentration in a range of 0.005-10 M, preferably 0.075-7.5 M, preferably 0.1-5 M, preferably 0.2-2 M, preferably 0.4-1 M, preferably 0.5-0.8 M.

In one embodiment, a molar ratio of a total amount of the amine starting material to CS$_2$ is in a range of 1:2 to 4:1, preferably 2:3 to 3:1, preferably 1:1 to 2:1. In a related embodiment, a molar ratio of CS$_2$ to the oxidizing agent is in the range of 1:2 to 2:1, preferably 2:3 to 3:2, preferably 1:1.2 to 1.2:1, or about 1:1.

The reaction mixture may be agitated (e.g., using an agitator, a vortexer, a rotary shaker, a magnetic stirrer, a centrifugal mixer, an overhead stirrer) at a temperature in a range of −4-50° C., 0-40° C., 10-35° C., 15-30° C., or 20-25° C. for any amount of time sufficient for reacting, typically from 0.1 to 12 hours, preferably from 0.25 to 8 hours, preferably from 0.5 to 4 hours, preferably from 1 to 2 hours.

The progress of the reactions may be monitored by methods known to those of ordinary skill in the art, such as thin layer chromatography, gas chromatography, nuclear magnetic resonance, infrared spectroscopy, and high pressure liquid chromatography combined with ultraviolet detection or mass spectroscopy. The crude disulfiram derivatives of formula (I) may be isolated and purified by methods known to those of ordinary skill in the art, such as filtration through a celite containing cartridge, evaporating the reaction mixture to dryness, aqueous work-up, extraction with organic solvents, distillation, recrystallization, column chromatography, and high pressure liquid chromatography (HPLC) on normal phase or reversed phase. Preferred methods include column chromatography and recrystallization. The disulfiram derivative may be obtained as an oil. Alternatively, precipitation/crystallization of the disulfiram derivative may occur, and the precipitate/crystals may be collected using methods known to those of ordinary skill in the art such as filtration.

According to a second aspect, the present disclosure relates to a pharmaceutical composition containing the disulfiram derivative of formula (I) of the first aspect and a pharmaceutically acceptable carrier and/or excipient.

As used herein, a "composition" or a "pharmaceutical composition" refers to a mixture of the active ingredient with other chemical components, such as pharmaceutically acceptable carriers and excipients. One purpose of a composition is to facilitate administration of the derivative disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, one or more of the disulfiram derivatives represented by formula (I), salts thereof, solvates thereof, tautomers thereof, stereoisomers thereof, or any mixtures thereof. In some embodiments, other active ingredients in addition to the disulfiram derivatives of the current disclosure may be incorporated into a pharmaceutical composition, for example, a second active ingredient which is chemically distinct from the disulfiram derivatives.

In one or more embodiments, the disulfiram derivative of formula (I) of the pharmaceutical composition is selected from the group consisting of

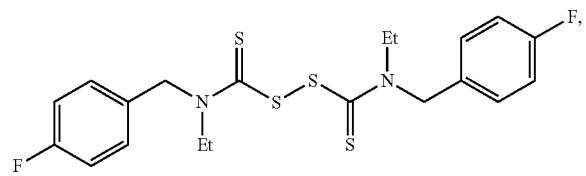 [SMILES: CCN(Cc1ccc(F)cc1)C(=S)SSC(=S)N(CC)Cc1ccc(F)cc1]

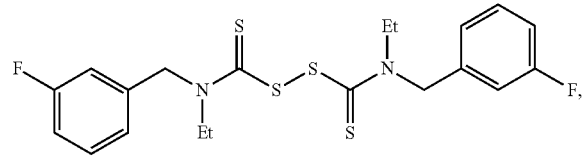

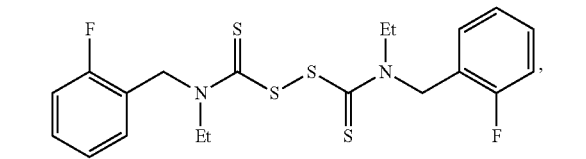

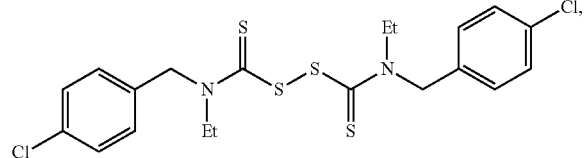

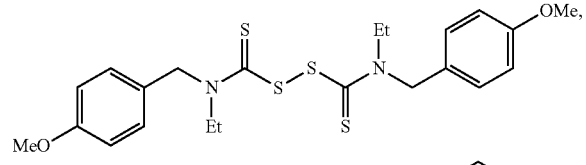

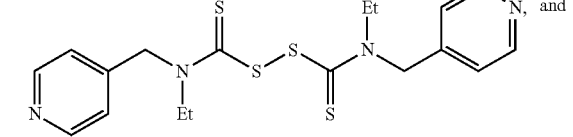

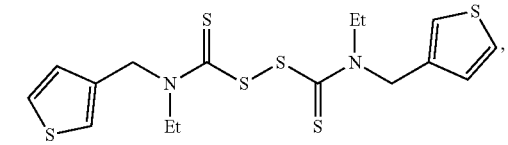

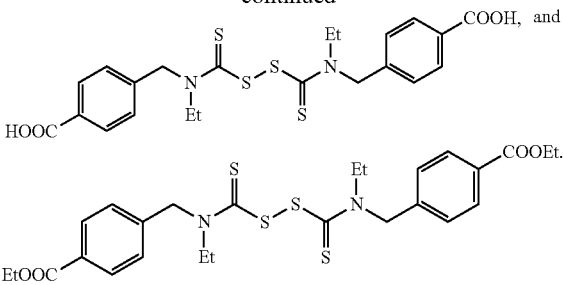

More preferably, the disulfiram derivative of formula (I) of the pharmaceutical composition is

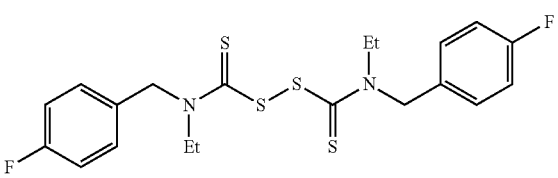

When the disulfiram derivatives are administered as pharmaceuticals, to humans and animals, they can be given per se or as a pharmaceutical composition containing the active ingredient(s) in combination with a pharmaceutically acceptable carrier and/or excipient. The pharmaceutical composition may contain at least 0.0001 wt. %, at least 0.001 wt. %, at least 0.01 wt. %, at least 0.05 wt. %, at least 0.1 wt. %, at least 0.5 wt. %, at least 5 wt. %, at least 10 wt. %, at least 15 wt. %, at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 95 wt. %, at least 99 wt. %, or at least 99.9 wt. % of the disulfiram derivative of formula (I) relative to a total weight of the pharmaceutical composition. For example, when formulated as a solution, the pharmaceutical composition may contain 0.1-100 µM of the disulfiram derivative of formula (I) relative to a total volume of the pharmaceutical composition, preferably 0.5-50 µM, preferably 1-45 µM, preferably 2-40 µM, preferably 3-35 µM, preferably 4-30 µM, preferably 5-25 µM, preferably 6-20 µM, preferably 7-15 µM, preferably 8-12 µM, preferably 10-11 µM of the disulfiram derivative relative to a total volume of the pharmaceutical composition.

In some embodiments, the active ingredient of the current disclosure. e.g., the disulfiram derivative of formula (I), a salt thereof, a solvate thereof, a tautomer thereof, a stereoisomer thereof, or any mixtures thereof, provides utility as an inhibitor against ALDH1a1 and/or MAGL. In some embodiments, the ability of the active ingredient to inhibit activity of the enzyme may be determined by contacting the pharmaceutical composition with the enzyme and then performing enzyme inhibition assays. Methods of such assays include, but are not limited to, Resazurin assay (e.g., diaphorase/resazurin assay), 4-nitrophenyl acetate assay, fluorescence-based fatty acid amide hydrolase inhibitor assay, sulforhodamine-B (SRB) assay, ATP test, Calcein AM assay, clonogenic assay, ethidium homodimer assay, Evans blue assay, 2',7'-dichlorofluorescin diacetate (DCFDA) or 2',7-dichlorodihydrofluorescein diacetate (H2DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, trypan blue assay, 4',6'-diamidino-2-phenylindole (DAPI) assay, TUNEL assay, a fluorochrome-labeled inhibitors of caspases (FLICA)-based assay, primary (1°) colonosphere formation assay, thioredoxin reductase assay, 20S proteasome activity assay, and in vitro scratch assay (for cell migration analysis). In one preferred embodiment, the enzyme inhibition assay is performed using 4-nitrophenylacetate and/or Fatty Acid Amide Hydrolase Inhibitor Screening Assay Kit, available from Cayman, Ann Arbor, Mich., USA. In another preferred embodiment, diaphorase/resazurin assay is used.

In some embodiments, other active ingredients in addition to the disulfiram derivatives of the current disclosure may be incorporated into the pharmaceutical composition. In one embodiment, the pharmaceutical composition includes an additional active ingredient that is chemically distinct from the disulfiram derivative of formula (I), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional active ingredient may be an anticancer agent and may include, but is not limited to, at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, other non-cancerous proliferative disorders that may also be treated by the currently disclosed pharmaceutical composition include, but are not limited to, neurodegeneration diseases, metabolic disorders such as obesity and diabetes, cardiovascular disorders, psychiatric diseases, traumatic brain injury, pain, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis.

The active ingredient of the current disclosure (e.g., disulfiram derivatives) may also exhibit other therapeutic activities such as anti-inflammatory, antioxidant, antimicrobial (e.g. antibacterial, antifungal, antiviral, antimycobacterial), pesticidal, as well as antimalarial efficacies.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Some examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutical composition contains 0.1 to 99.9999 wt. %, preferably 1 to 99.999 wt. %, preferably 5 to 99.99 wt. %, preferably 10 to 99.9 wt. %, preferably 15 to 99 wt. %, preferably 20 to 90 wt. %, preferably 30 to 85 wt. %, preferably 40 to 80 wt. %, preferably 50 to 75 wt. %, preferably 60 to 70 wt. % of the pharmaceutically acceptable carrier and/or excipient relative to a total weight of the pharmaceutical composition.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per as, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration.

The active ingredient(s) can be dissolved in aqueous or non-aqueous carriers including, but not limited to, water, ethanol, benzyl alcohol, DMSO, polyethylene glycol, propylene glycol, ethanol, corn oil, cottonseed oil, peanut oil, sesame oil, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Formulations of the pharmaceutical compositions of the disclosure for rectal or vaginal administration may be presented as a suppository, which may be prepared by mixing one or more disulfiram derivatives with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredient(s).

Formulations of the pharmaceutical compositions which are suitable for vaginal administration also include pessaries, tampons, creams, gels, pastes, foams or spray formulations containing such carriers as are known in the art to be appropriate.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the presently disclosed derivative(s), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to another aspect, the present disclosure relates to a method of treating an ALDH1a1 and/or MAGL mediated disease or disorder in a subject. The method involves administering a therapeutically effective amount of one or more disulfiram derivatives of formula (I) per se, or the pharmaceutical composition described above to a subject in need of therapy.

In one or more embodiments, the ALDH1a1 and/or MAGL mediated disease or disorder is cancer. The disclosed method of the current aspect is for treating cancer of the blood, stomach, breast, colon, brain, bladder, lung, cervix, ovary, rectum, pancreas, skin, prostate gland, spleen, liver, kidney, head, neck, testicle, bone, bone marrow, thyroid gland, or central nervous system. In some embodiments, the ALDH1a1 and/or MAGL mediated disease or disorder is selected from the group consisting of colon cancer, pancreatic cancer, nasopharyngeal carcinoma, thyroid cancer, prostate cancer, ovarian cancer, head and neck squamous cell carcinoma, lung cancer, hepatocellular carcinoma, leukemia, brain tumors, estrogen-dependent growth of uterine fibroids, and breast cancer. In one preferred embodiment, the cancer is at least one selected from the group consisting of breast cancer, brain cancer (e.g., glioblastoma), and pancreatic cancer. In another preferred embodiment, the cancer is at least one selected from the group consisting of prostate cancer, colorectal cancer, liver cancer (e.g., hepatocellular carcinoma), and nasopharyngeal cancer.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The currently disclosed method may treat other non-cancerous ALDH1a1 mediated diseases or disorders including, but not limited to, neurodegenerative diseases such as Parkinson's Disease and Alzheimer's Disease, Huntington's disease, multi-infarct dementia, amyotrophic lateral sclerosis (ALS), peripheral artery disease; cardiovascular disorders such as angina, heart failure, insensitivity to nitroglycerin in angina and heart failure, hypertension, and heart disease; metabolic disorders such as diabetes (Type 1, Type 2 diabetes), and obesity; inflammations such as atherosclerosis, ischaemic heart disease, acne vulgaris, asthma, autoimmune diseases, auto-inflammatory diseases, celiac disease, chronic prostatitis, glomerulonephritis, hypersensitivities, inflammatory bowel disease, pelvic inflammatory disease, reperfusion injury, rheumatoid arthritis, sarcoidosis, transplant rejection, vasculitis, and interstitial cystitis; and Crohn's disease.

Additionally, the currently disclosed method may treat other non-cancerous MAGL mediated diseases or disorders including, but not limited to, neurodegenerative diseases (as noted above); psychiatric diseases such as melancholic depression, atypical depression, dysthymia, postpartum depression, anxiety disorder, obsessive compulsive disorder, addiction disorder, alcohol use disorder, opioid use disorder, amphetamine use disorder, nicotine use disorder, cocaine use disorder, panic disorder, post-traumatic stress disorder (PTSD), major depressive disorder (MDD), treatment-resistant depression (TRD), suicidal ideation and suicide attempts, bipolar disorder, schizophrenia (e.g., positive symptom, negative symptom, cognitive impairment), cyclothymic disorder, obsessive-compulsive disorder (OCD), generalized anxiety disorder (GAD), social anxiety disorder, gambling disorder, eating disorder, anorexia nervosa, bulimia nervosa, binge-eating disorder, and attention deficit hyperactivity disorder (ADHD); traumatic brain injury, cerebral apoplexy, cluster headaches, migraine headaches, and nausea; and pain such as inflammatory pain, cancer pain, and neuropathic pain.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In some embodiments, the subject is a person who is predisposed to cancer, e.g. a person with a family history of cancer. For example, women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) have certain inherited mutated genes (e.g. mutated RNASEL, mutated BRCA1 and/or mutated BRCA2), (ii) had inflammation in the prostate, and/or (iii) are obese are at a higher risk of contracting prostate cancer.

In another embodiment, the subject refers to a cancer patient who has been previously treated and/or administered with an aldehyde dehydrogenase (ALDH) inhibitor and developed resistance to the ALDH inhibitor. In another embodiment, the subject refers to a cancer patient who has been previously administered and/or treated with a MAGL inhibitor and developed resistance to the MAGL inhibitor.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In a preferred embodiment, the active ingredient and/or the pharmaceutical composition described herein are administered orally.

With respect to the ALDH1a1 mediated diseases or disorders, the pharmaceutical composition administered preferably comprises the disulfiram derivative of formula (I), or a salt thereof, a solvate thereof, a tautomer thereof, or a stereoisomer thereof, in which $R_1$ and $R_2$ are each independently selected from the group consisting of —$CH_2CH_2COOH$,

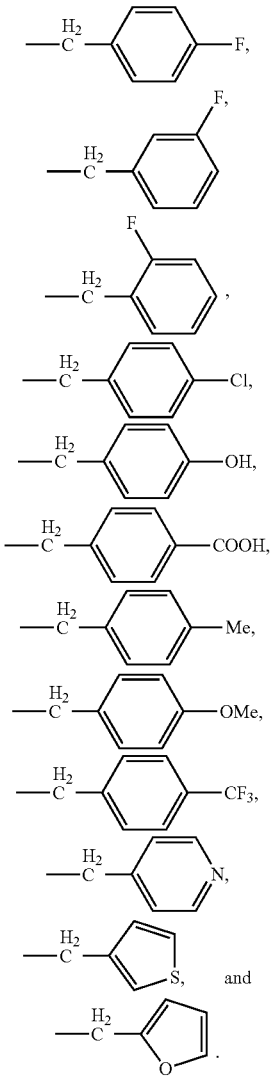

In a most preferred embodiment, the pharmaceutical composition administered comprises a disulfiram derivative which is selected from the group consisting of

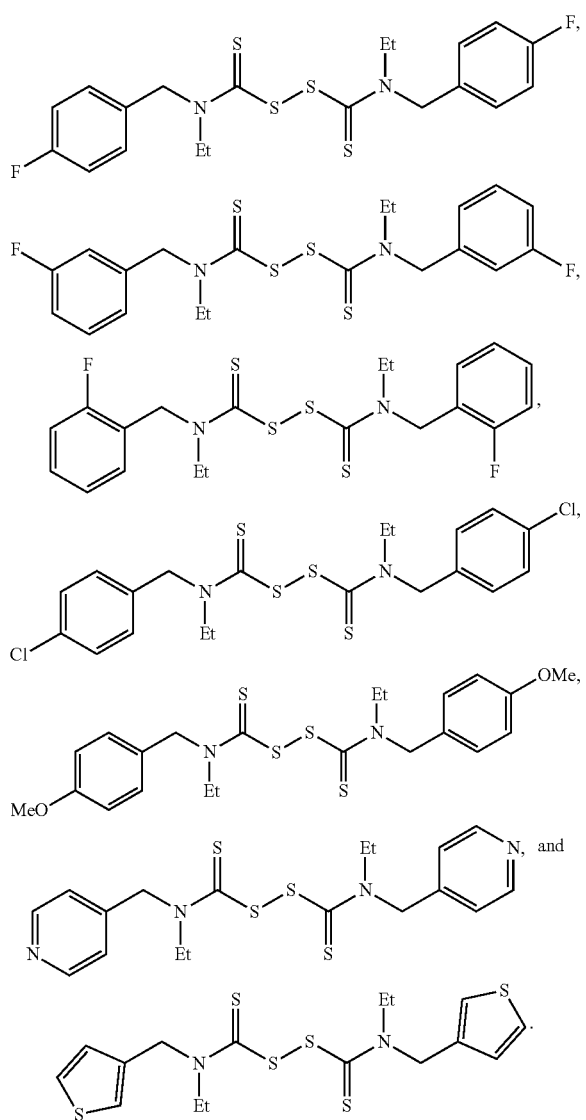

With respect to the MAGL mediated diseases or disorders, the pharmaceutical composition administered preferably comprises the disulfiram derivative of formula (I), or a salt thereof, a solvate thereof, a tautomer thereof, or a stereoisomer thereof, in which $R_1$ and $R_2$ are each independently selected from the group consisting of —CH$_2$CH$_2$COOH, —CH$_2$CH$_2$COOEt,

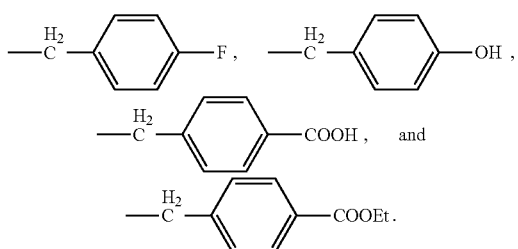

In a most preferred embodiment, the pharmaceutical composition administered comprises a disulfiram derivative which is selected from the group consisting of

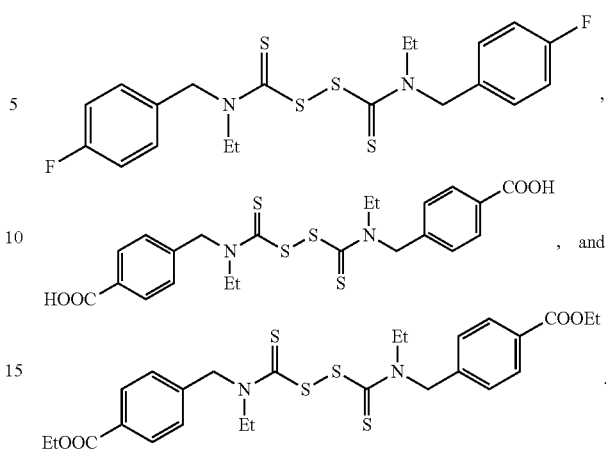

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study.

Regarding the ALDH1a1 mediated diseases or disorders, an effective amount of the disulfiram derivative disclosed herein in a range of 0.01-100 mg/kg, preferably 0.1-50 mg/kg, more preferably 1-10 mg/kg is administered per body weight of the subject. However, in certain embodiments, the effective amount of the derivative is less than 0.01 mg/kg or greater than 10 mg/kg.

Regarding the MAGL mediated diseases or disorders, an effective amount of the disulfiram derivative disclosed herein in a range of 0.1-500 mg/kg, preferably 1-100 mg/kg, more preferably 5-20 mg/kg is administered per body weight of the subject. However, in certain embodiments, the effective amount of the derivative is less than 0.1 mg/kg or greater than 500 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

A treatment method may comprise administering a pharmaceutical composition containing the derivative of the current disclosure in any of its embodiments as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other diseases/disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments, the method further comprises measuring a concentration of a biomarker and/or detecting a mutation in a biomarker before and/or after the pharmaceutical composition comprising the disulfiram derivative of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for prostate cancer include, without limitation, tPSA, fPSA, p2PSA, HOXC6 DLX1, GSTP1, RASSF1, and APC. The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the disulfiram derivative of the present disclosure by at least 5%, at least 10%, or at least 30%, up to 50%, up to 60%, or up to 80% of an initial effective amount that is in a range of 0.1-500 mg/kg per body weight of the subject. The increased effective amount may be in a range of 0.105-900 mg/kg, preferably 1-500 mg/kg, more preferably 10-250 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing the disulfiram derivatives of formula (I) and uses thereof, and are not intended to limit the scope of the claims.

Example 1

Exemplary Synthesis of Thiuram Disulfides (Table 1)

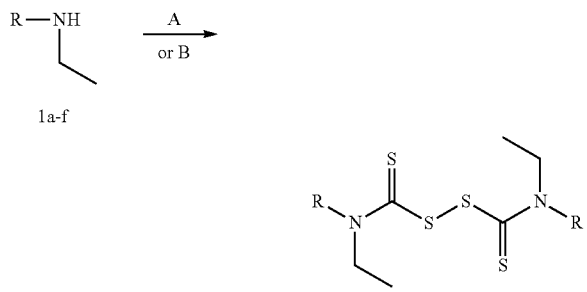

Method A): $CS_2$, $CBr_4$, DMF, RT (for 2a-c)
Method B): $CS_2$, $NaNO_2$, NaOH, water, 0° C. (for 2d-f)

TABLE A/B

| No. | R | Yield |
|---|---|---|
| 2a | PhCH₂— | 49% |
| 2b | 4-F-C₆H₄-CH₂— | 40% |
| 2c | 4-HO-C₆H₄-CH₂— | 95% |
| 2d | 4-HOOC-C₆H₄-CH₂— | 38% |
| 2e | HO(O)CCH₂CH₂— | 11% |
| 2f | HOCH₂CH₂— | 10% |

Thiuram disulfides I-2a to I-2c were synthesized from the corresponding secondary amines, as shown above. See Mario, S., Hosler, John F. N,N'-dicarboxymethyl thiuram disulfides. U.S. Pat. No. 2,784,223; and Wiggins H L, Wymant J M, Solfa F, et al. Disulfiram-induced cytotoxicity and endo-lysosomal sequestration of zinc in breast cancer cells. *Biochem Pharmacol.* 2015; 93: 332-342, each incorporated herein by reference in their entirety. As shown above, compounds I-2a to I-2c were synthesized by Method A. Compounds I-2d to I-2f were synthesized by Method B.

Typically, two equivalents of the amines were treated with one equivalent of carbon disulfide in an ice-water bath. Oxidation of the resulting product by one equivalent of carbon tetrabromide ($CBr_4$) yielded the desired disulfiram analogues I-2a to I-2c (Method A).

Method A:

$CS_2$ (2.0 mmol) was added to a solution of amine (1-1a to I-1c) (4 mmol) in DMF (4 mL) in an ice-water bath. The mixture was stirred for 5 min. $CBr_4$ (2 mmol) was then added, and the mixture was stirred at RT for further 30 min. The mixture was poured into ice-water (40 mL) with stirring and then extracted with $CH_1Cl_2$ for I-2a and I-2b and with $CHCl_3$ for I-2c. The organic layer was dried over $MgSO_4$, concentrated under vacuum, and subjected to column chromatography on silica gel to give I-2a to I-2c.

Conversely, the polar disulfiram analogues I-2d to I-2f were obtained by treating the corresponding amine with carbon disulfide in an aqueous solution of sodium hydroxide. Treatment of this mixture with sodium nitrite afforded the desired compounds (Method B).

Method B:

Amine I-1d to 1-1f (5.57 mmol) was added to a cold solution of sodium hydroxide 2.20 g (5.57 mmol.) in 4.32 mL of water. The solution was cooled to 0-5° C. in an ice-water bath and stirred at that temperature while 0.34 mL (5.57 mmol) of carbon disulfide was added gradually. The mixture was then stirred at the same temperature for 2 h. Sodium nitrite (0.38 g; 5.57 mmol) and 0.45 mL methanol were successively added and the mixture was stirred for 10 min. Hydrochloric acid (1 mL) was then added gradually (to pH 1) while the mixture is kept below 5° C. and stirred vigorously for 15 min. For I-2d, the suspension was filtered and rinsed twice with 10 mL water and dried under vacuum over phosphorus pentoxide in a desiccator. For I-2e and I-2f, the suspension was extracted twice with diethyl ether (2×10 ml). The combined organic layers were dried over $NaSO_4$ and concentrated under vacuum. The residual oil obtained was then purified by chromatography to give I-2e and I-2f.

Example 2

Exemplary Synthesis of Thiuram Disulfides (Table II)

Synthesis procedures of compounds II-2g and II-2l (see Table II below) are described as follows. $CS_2$ (2.0 mmol) was added to a solution of amine (1) (4 mmol) in DMF (4 mL) in an ice-water bath. The mixture was stirred for 5 min. $CBr_4$ (2 mmol) was then added, and the mixture was stirred at RT for further 30 min. The mixture was poured into ice-water (40 mL) with stirring and then extracted with 2×40 mL $CH_2Cl_2$. The organic layer was dried over $MgSO_4$, concentrated under vacuum, and purified by to column chromatography on silica gel to give the desired products II-2g and II-2l.

Example 3

Synthesis of Amine Starting Materials

Amine (II-1g)

As shown in Reaction Scheme 2 below, Amine (II-1g) was obtained by amination of 3-bromopropanoate (II-3) by benzylethylamine. Debenzylation of amine (II-4) by reductive cleavage over palladium metal with molecular hydrogen yielded the desired amine (II-1g).

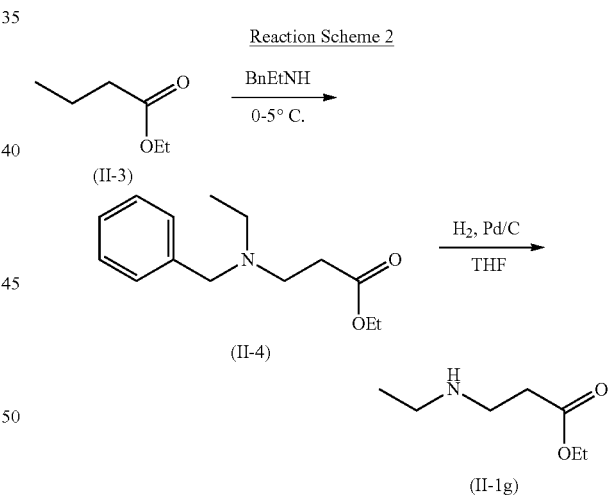

Reaction Scheme 2

Ethyl 3-(benzyl(ethyl)amino)propanoate (II-4):

As shown in Reaction Scheme 2 above, to 2.6 mL (20 mmol) of ethyl 3-bromopropanoate (II-3) cooled to (0-5° C.) was added dropwise during 5 min 6 mL (40 mmol) of benzylethylamine under vigorously stirring. After few minutes, the solution solidified. To this solid was added 30 mL of diethyl ether. The suspension was stirred vigorously for 5 min, filtered and the filtrate was concentrated in vacuo to give 3.6 g of an oil which is engaged in the next step without further purification, Yield: 76% (light yellow oil), FT-4R: 3028, 2972, 2935, 2802, 1732, 1452, 1369, 1247, 1192, 1161, 1045, 1028 cm⁻¹. ¹HNMR (400 MHz, $CDCl_3$): 1.03

(3H, t, $^3J$=7.2 Hz), 1.23 (3H, t, $^3J$=7.2 Hz), 2.40-2.56 (4H, m), 3.58 (2H, s), 4.11 (2H, q, $^3J$=7.2 Hz), 7.20-7.35 (5H, m).

Ethyl 3-N-ethylaminopropanoate (II-1g):

As shown in Reaction Scheme 2, to 2.55 g (10.8 mmol.) of ethyl 3-N-ethylbenzylaminopropanoate diluted in 50 mL of THF was added cautiously 1 g of palladium 10% on carbon. The suspension was hydrogenated at atmospheric pressure and room temperature for 6 hours. The reactional medium was degassed and the suspension was filtered on a pad of celite to remove the catalyst. The filtrate is concentrated in vacuo (bath temperature at 35° C. to avoid amidification) to give 1.48 g of compound (II-1g) as an oil. Yield: 94% (light yellow oil). FT-IR: 3313, 2968, 2937, 2827, 1730, 1446, 1373, 1186, 1141, 1026 cm$^{-1}$. $^1$H NMR (400 MHz, CDCl$_3$): 1.11 (3H, t, 3J=7.2 Hz), 1.26 (3H, t, $^3J$=7.2 Hz), 2.52 (2H, t, $_3$J=6.4 Hz), 2.66 (2H, q, $^3J$=7.2 Hz), 2.89 (2H, t, $^3J$=6.4 Hz), 4.14 (2H, q, $^3J$=7.2H).

Amine (II-1l)

As shown in Reaction Scheme 3 below, amine (II-1l) was obtained by reductive amination of commercial 4-formylbenzoic acid (II-5) using 2 equivalents of ethylamine in methanol and reducing the intermediate imine by sodium borohydride. The obtained amine (II-1k) was then esterified in refluxing ethanol to give the aimed amine (II-1l).

Reaction Scheme 3

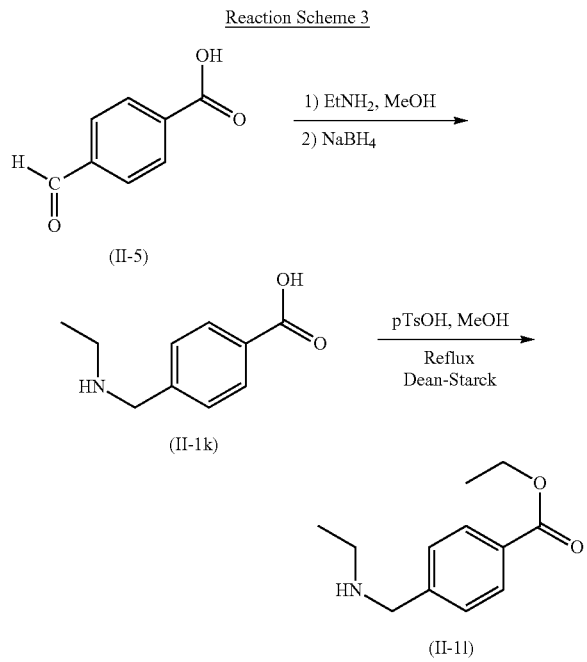

4-((ethylamino)methyl)-benzoic acid (II-1k):

To a cold solution of 4.50 g (30 mmol) of commercial 4-formylbenzoic acid dissolved in 50 mL of dry methanol was added 20 g of molecular sieves (4A) and 67 mL of ethylamine 0.9 M in methanol. The suspension was stirred 14 hours at R.T. and filtered. To the cold filtrate was added 2.2 g (30 mmol.) of sodium borohydride by portions and the solution was stirred 15 hours. The mixture was concentrated to dryness in vacuo and cold water was added. To the aqueous layer was added HCl conc. (5 mL) to reach pH 7.15. The mixture was then concentrated to dryness under vacuum and the residual solid was extracted twice with 150 mL of methanol. The methanolic solution was dried on sodium sulphate, filtered and then concentrated to dryness under vacuum to give 4.80 g of white solid corresponding to (II-1k) (zwitterionic form). Yield: 89% (white solid). FT-IR: 3356, 3037, 2976, 1589, 1543 cm$^{-1}$. 1H NMR (400 MHz, D$_2$O): 1.32 (3H, t, 3J=7.6 Hz), 3.15 (2H, q, $^3J$=7.6 Hz), 4.24 (2H, s), 7.48 (2H, d, $^3J$=8.4 Hz), 7.85 (2H, d, $^3J$=8.4 Hz).

Ethyl 4-((ethylamino)methyl)-benzoate (II-1l):

A suspension of 2.61 g (14.56 mmol) of (II-1k) and of 3.06 g (17.77 mmol) of p-toluenesulfonic acid in a mixture 100 mL of dry toluene and 100 mL of ethanol was heated at reflux for 6 hours in a round bottom flask equipped with a Dean-Stark apparatus. After cooling the obtained solution, 50 mL of diethyl ether was added, and the suspension was stirred 15 min, then filtered and washed 3 times with diethyl ether. The solid was solubilized in 50 mL cold water and 25 mL of NaOH 1N aq. was added dropwise. The aqueous solution was extracted 3 times with 10 mL of DCM. The combined organic layers are dried over Na$_2$SO$_4$ and concentrated in vacuo (bath temperature 35° C. to avoid amidification) to give 0.63 g of compound (II-1l) as a light yellow oil. Yield: 20% (light yellow oil). FT-IR: 3313, 2966, 2933, 1712, 1610, 1271, 1101, 1020, 752 cm$^{-1}$. $^1$H NMR (400 MHz, CDCl$_3$): 1.11 (3H, t, $^3J$=7.2 Hz), 1.26 (3H, t, $^3J$=7.2 Hz), 2.52 (2H, t, $^3J$=6.4 Hz), 2.66 (2H, q, $^3J$=7.2 Hz), 2.89 (2H, t, $^3J$=6.4 Hz), 4.14 (2H, q, $^3J$=7.2 Hz).

Example 4

Characterizations

Compounds in Table 1:

bis(N-benzylethylthiocarbamoyl)disulfide (I-2a)

Column chromatography: Silica Gel, CHCl$_3$-PE (90/10). Yield: 49% (viscous oil). IR: 3028.34, 2974.33, 1481.38, 1413.87, 1350.22, 1240.27, 1190.12 cm$^{-1}$. $^1$H NMR (400 MHz, CDCl$_3$): 1.28 (3H, bs), 1.42 (3H, bs), 4.01 (4H, bs), 5.15-5.45 (4H, bs), 7.2-7.5. (10H, m). $^{13}$C NMR (100 MHz, CDCl$_3$): 11.20, 13.29, 47.26, 52.12, 55.85, 59.59, 127.53, 127.77, 127.89, 128.28, 128.85, 128.98, 129.06, 134.61, 135.27, 193.82, 195.36. HR-MS (ESI$^+$) m/z [M+1] calculated: 421.0901, found: 421.0892.

bis(N-4-Fluorobenzylethylthiocarbamoyl)disulfide (I-2b)

Column chromatography: Silica Gel, CHCl$_3$-PE (90/10). Yield: 40% (viscous oil). IR: 2976.26, 1602.90, 1508.38, 1481.38, 1408.08, 1219.05, 1157.33 cm$^{-1}$. $^1$H NMR (400 MHz, CDCl$_3$): 1.27 (3H, bs), 1.44 (3H, bs), 4.00 (4H, bs), 5.1-5.45 (4H, bs), 6.95-7.50 (8H, m). $^{13}$CNMR (100 MHz, CDCl$_3$): 11.22, 13.33, 47.32, 52.08, 55.14, 58.92, 115.6, 129.56, 130.32, 131.04, 161.28, 163.73, 193.62, 195.45. HR-MS (ESI$^+$) m/z [M+1] calculated: 457.0712, found: 457.0702.

bis(N-4-hydroxybenzylethylthiocarbamoyl)disulfide (I-2c)

Column chromatography: Silica Gel, CH$_2$Cl$_2$-MeOH (95/5). Yield: 95% (viscous oil). IR: 3311.89, 2931.90, 2359.02, 1651.12, 1610.61, 1512.24, 1483.31, 1415.80, 1348.29, 1168.90, 1101.39, 993.37, 914.29 cm$^{-1}$. $^1$H NMR (400 MHz, CD$_3$OD): 1.19 (3H, bs), 1.37 (3H, bs), 3.96 (4H, bs), 5.14-5.27 (4H, bs), 6.74-7.31 (8H, m). $^{13}$C NMR (400 MHz, CD$_3$OD): 11.30, 11.49, 47.86, 52.71, 56.39, 60.03, 116.36, 116.59, 126.92, 127.76, 129.99, 130.34, 130.48, 147.92, 138.25, 158.52, 194.24, 195.85. HR-MS (ESI$^+$) m/z [M+1] calculated: 453.0799, found: 453.0788.

bis(N-4-carboxybenzylethylthiocarbamoyl)disulfide (I-2d)

Yield: 38%. Melting point: 220° C. IR: 3475, 2976, 1688, 1612, 1481, 1408, 1282, 1242 cm$^{-1}$. $^1$H NMR (400 MHz, DMSO-d6): 1.18-1.38 (6H, m), 4.00 (4H, bs), 5.30-5.42 (4H, m), 7.36-7.51 (4H, m), 7.88-7.97 (4H, m). $^{13}$C NMR (100 MHz, DMSO-d6): 11.04, 13.24, 47.98, 52.46, 55.02, 58.82, 127.23, 129.52, 129.74, 130.98, 131.54, 139.67, 140.14, 167.36, 192.37, 193.69. HR-MS (ESI$^-$) m/z [M−1] calculated: 507.0541, found: 507.0543.

bis(N-carboxylethylethylthiocarbamoyl)disulfide (I-2e)

Column chromatography: Silica Gel, CH$_2$Cl$_2$-MeOH (98/2%). Yield: 11% (viscous oil) IR: 3091, 2974, 1707, 1487, 1408, 1381, 1278, 1184, 1165, 1103 cm$^{-1}$. $^1$H NMR (400 MHz, CDCl$_3$): 1.10-1.60 (6H, m), 2.60-3.25 (4H, bs), 3.30-4.35 (8H, m), 7.79 (2H, bs). $^{13}$C NMR (100 MHz, CDCl$_3$): 11.48, 13.27, 13.53, 14.25, 31.05, 32.75, 44.59, 49.03, 49.31, 52.23, 177.11, 177.22, 193.67, 194.53. HR-MS (ESI$^-$) m/z [M−1] calculated: 383.0233. found: 383.0228.

bis(N-hydroxyethylethylthiocarbamoyl)disulfide (I-2f)

Column chromatography: Reverse phase C18, ACN/H$_2$O (50/50). Yield: 10% (viscous oil). IR: 3333, 2974, 2931, 2872, 1487, 1413, 1350, 1280, 1263, 1188, 1041, 926 cm$^{-1}$. $^1$H NMR (400 MHz, CDCl$_3$): 1.15-1.60 (6H, m), 2.70 (2H, bs), 3.90-4.25 (12H, m). $^{13}$C NMR (400 MHz, CDCl$_3$): 11.19, 13.23, 50.10, 53.58, 54.47, 58.89, 60.17, 193.54, 194.77. HR-MS (ESI$^+$) m/z [M+1] calculated: 329.0486, found: 329.0486.

Compounds in Table II:

bis(N-ethoxycarbonylethylethylthiocarbamoyl)disulphide (II-2g):

Column chromatography Silica Gel, CH$_2$Cl$_2$-MeOH (100/0% to 98/2%), Yield; 34% (viscous oil). IR: 2978, 2934, 1726, 1487, 1415, 1373, 1279, 1180, 1163 cm$^{-1}$. $^1$H NMR (400 MHz, CDCl$_3$): 1.27 (3H, bs), 1.48 (3H, bs), 2.86 (2H, bs), 3.01 (2H, bs), 4.05-4.30 (12H, bs). $^{13}$C NMR (100 MHz, CDCl$_3$): 11.46, 13.50, 14.26, 14.33, 31.29, 33.03, 47.94, 49.18, 52.55, 52.85, 60.94, 61.23, 170.73, 171.72, 193.19, 193.51. HR-MS (ESI$^+$) m/z [M+1] calculated: 441.1010, found: 441.1015.

bis(N-4-ethoxycarbonylbenzylethylthiocarbamoyl)disulphide (II-2l):

Column chromatography Silica Gel, CH$_2$Cl$_2$ (100%). Yield: 23% (viscous oil). IR: 3059, 2976, 1710, 1610, 1481, 1458, 1408 cm$^{-1}$. $^1$H NMR (400 MHz, CDCl$_3$): 1.20-1.50 (12H, m), 4.02 (4H, bs), 4.37 (4H, q, 3J=7.2 Hz), 5.20-5.50 (4H, m), 7.30-7.55 (4H, m), 7.95-8.15 (4H, m). $^{13}$C NMR (100 MHz, CDCl$_3$): 11.13, 11.31, 13.44, 14.43, 47.82, 52.53, 55.58, 59.47, 61.13, 127.54, 130.15, 139.64, 140.28, 193.94, 195.63. HR-MS (ESI$^+$) m/z [M+1] calculated: 565.1323, found: 565.1321.

Example 5

ALDH Assay

ALDH catalyzes the oxidation of acetaldehyde to acetic acid while reducing NAD+ to NADH. The formation of NADH is fluorescently detected using diaphorase/resazurin system. Diaphorase utilizes NADH formed from ALDH reaction to produce the fluorescent molecule resorufin from resazurin. See Davis, M. I.; Shen, M.; Simeonov, A.; Hall, M. D., Diaphorase Coupling Protocols for Red-Shifting Dehydrogenase Assays. Assay Drug Dev Technol 2016, 14 (3), 207-12; and Lam, J. P.; Mays, D. C.; Lipsky, J. J., Inhibition of recombinant human mitochondrial and cytosolic aldehyde dehydrogenases by two candidates for the active metabolites of disulfiram. *Biochemistry* 1997, 36 (44), 13748-54, each incorporated herein by reference in their entirety.

Example 6

ALDH Assay Reagents and Consumables

The reagent ALDH1a1 is from R&D Systems (Minneapolis, MN). ALDH2 is from Prospect Bio (East Brunswick, NJ). Acetaldehyde is from Cayman Chemicals (Ann Arbor, MI). NAD$^+$, and Resazurin sodium salt are from Sigma (St. Louis, MO). Diaphorase is from Reaction Biology (Malvern PA). Zaba micro spin columns are from ThermoFisher scientific (Waltham, MA). Corning 3573, 384 Well Black Flat Bottom Microplate are VWR (Radnor, PA). Enzymes were desalted to get rid of DTT using Zeba micro spin desalting columns (7K MWCO, 75 ul volume) following manufacturer's protocol. 10 ul enzyme and 3 ul reaction buffer (as stacker) were added to each desalting column. Desalted samples from each enzyme were pooled together and placed in ice until use. Reaction buffer (50 mM sodium pyrophosphate buffer at pH 8.8, 0.01% Brij35) degassed using vacuum for 10 mins until no visible air bubbles were seen.

Example 7

ALDH Assay Protocols

5 µl of enzyme (150 nM for ALDH1a1 and 200 nM for ALDH2 in reaction buffer) were delivered to assay wells in coming black, 384 well plate. 5 µl of reaction buffer was delivered to 'no enzyme' background control wells. Test compounds were prepared in 100% DMSO by serial dilution in 100× of assay concentration. After adding the test compounds, reaction plate was centrifuged briefly in 1200 rpm, then incubated for 20 min at room temperature, to pre-incubate enzyme and compounds. 5 µl of substrate solution (reaction buffer containing 250 µM Acetaldehyde, 500 µM NAD$^+$ for ALDH1a1 and 100 µM Acetaldehyde, 500 µM NAD$^+$ in the for ALDH2) were then delivered to assay wells. Reaction plate was briefly centrifuged and sealed with a plastic film to limit evaporation. After incubation at room temperature for 60 min, 10 µl of detection reagent (15 µg/ml diaphorase, 30 µM resazurin prepared in the degassed reaction buffer) was added. Reaction plate was briefly centrifuged and incubated for 10 minutes at room temperature in the dark. Fluorescent signal from resorufin was measured by Perkin Elmer Envision at Ex/Em=535/590 nm.

Example 8

Inhibitory Effects Against ALDH1a1 and ALDH2

The inhibitory activities of the synthesized compounds I-2a-f and their commercially available analogues I-2g-m were evaluated in-vitro against ALDH1a1 and ALDH2 (see Table I below).

TABLE I*

Inhibition of ALDH1a1 and ALDH2 by compounds I-2a-I-2m and 3-5

$$R^1\text{-}N(R^2)\text{-}C(=S)\text{-}S\text{-}S\text{-}C(=S)\text{-}N(R^2)\text{-}R^1$$

I-2a-I-2m

| Compound | $R^1$ | $R^2$ | $IC_{50}$ (μM) ± SE (ALDH1a1) | $IC_{50}$ (μM) ± SE (ALDH2) |
|---|---|---|---|---|
| Disulfiram | Et | Et | 0.13 ± 0.10 | 3.40 ± 0.71 |
| I-2a | Et | C₆H₅-CH₂— | 0.27 ± 0.10 | NI |
| I-2b | Et | 4-F-C₆H₄-CH₂— | 0.17 ± 0.06 | NI |
| I-2c | Et | 4-HO-C₆H₄-CH₂— | 0.21 ± 0.04 | 10.89 ± 0.61 |
| I-2d | Et | 4-HOOC-C₆H₄-CH₂— | 2.95 ± 1.52 | 99.36 ± 0.64 |
| I-2e | Et | HO(O)OCH₂CH₂— | 0.15 ± 0.14 | 0.85 ± 0.55 |
| I-2f | Et | HOCH₂CH₂— | 2.54 ± 1.15 | 25.69 ± 12.34 |
| I-2g | Et | Me | 0.02 ± 0.01 | 0.32 ± 0.04 |
| I-2h | (CH₃)₂CH— | (CH₃)₂CH— | 2.85 ± 1.00 | >100 |
| I-2i | CH₃CH₂CH₂CH₂— | CH₃CH₂CH₂CH₂— | 5.61 ± 2.51 | 72.60 ± 24.39 |
| I-2j | (CH₃)₂CHCH₂— | (CH₃)₂CHCH₂— | >100 | NI |
| I-2k | C₆H₅-CH₂— | C₆H₅-CH₂— | >100 | NI |
| I-2l | —CH₂CH₂CH₂CH₂CH₂— | | 0.06 ± 0.02 | 1.51 ± 0.22 |
| I-2m | —CH₂CH₂OCH₂CH₂— | | 0.04 ± 0.03 | 1.43 ± 0.32 |
| 3 Cysteamine•HCl | — | — | NI | NI |
| 4 Cysteamine•2HCl | — | — | >100 | NI |
| 5 N•Acetyl-l-Cysteine | — | — | NI | NI |

*The $IC_{50}$ is expressed as the mean of at least two independent experiments. NI: no inhibition seen at the tested conditions.

Disulfiram is a potent inhibitor of ALDH1a1. It showed an $IC_{50}$ in the submicromolar range, in agreement with values reported in the literature. See Lipsky J J, Shen M L, Naylor S. In vivo inhibition of aldehyde dehydrogenase by disulfiram. *Chem Biol Interact.* 2001; 130-132; 93-102, incorporated herein by reference in its entirety. As shown in Table I, replacing two of the four ethyl groups in disulfiram with benzyl motifs was well tolerated, especially if the phenyl rings were unsubstituted (I-2a) or substituted with small groups (I-2b-I-2c). Substituting the phenyl para position of I-2a with a carboxylic acid function (I-2d) resulted in a tenfold decrease in ALDH1a1 inhibitory activity, whereas introducing the carboxylate function directly onto the ethyl groups of disulfiram (I-2e) seemed to have no effect on the activity against ALDH1a1.

The carboxylate functions were introduced to limit the passage through the blood brain barrier, as disulfiram had been reported to have rare, but severe, central nervous system side effects. See Pajouhesh H, Lenz G R. Medicinal chemical properties of successful central nervous system drugs, *NeuroRx,* 2005; 2:541-553; and McConchie R D, Panitz D R, Sauber S R, Shapiro S. Disulfiram-induced de novo seizures in the absence of ethanol challenge. *J Stud Alcohol,* 1983; 44:739-743, each incorporated herein by reference in their entirety. Substituting the thiuram disulfide core of disulfiram with smaller alkyl groups (I-2g) improved its activity towards ALDH1a1. Similarly, the introduction of bulky alkyl groups, such as isopropyl (I-2h) or butyl (I-2l), significantly diminished inhibition activity. Furthermore, the bulkier isobutyl (I-2j) resulted in a complete loss of activity, as did replacement of all four ethyl groups with benzyl motifs (I-2k). Conversely, replacing the ethyl groups with cyclic structures (I-2l and I-2m) slightly improved the activity against ALDH1a1.

The selectivity of the developed molecules was assessed by evaluating their in-vitro inhibitory activity against the mitochondrial ALDH2. Disulfiram shows a modest selectivity, being tenfold more active against ALDH1a1 than ALDH2, and this difference was confirmed further in the present study. See Koppaka V, Thompson D C, Chen Y, et al.

Aldehyde dehydrogenase inhibitors: a comprehensive review of the pharmacology, mechanism of action, substrate specificity, and clinical application. *Pharmacol Rev.* 2012; 64:520-539; and Lipsky J J, Shen M L, Naylor S. In vivo inhibition of aldehyde dehydrogenase by disulfiram. *Chem Biol Interact.* 2001; 130-132:93-102, each incorporated herein by reference in their entirety. ALDH2 has a smaller substrate tunnel than that of ALDH1a1; therefore, ALDH2 was more sensitive to the size of the alkyl groups, as isopropyl (I-2h), butyl (I-2l) and isobutyl (I-2j) introductions led to a significant loss of the activity against ALDH2. By contrast, ALDH2 seemed to tolerate hydrophilic substitutions, such as hydroxyl (I-2c and I-2f) or carboxylate groups (I-2d and I-2e). Interestingly, the introduction of a phenyl group (I-2a) or a para fluorophenyl group (I-2b) resulted in a complete loss of the ALDH2 inhibitory activity. Therefore, compound I-2b showed the same activity as disulfiram against ALDH1a1, whereas it was completely inert against ALDH2.

Disulfiram inhibits ALDH1a1 by irreversible carbamylation of the catalytic Cys302 residue. See Koppaka V, Thompson D C, Chen Y, et al. Aldehyde dehydrogenase inhibitors: a comprehensive review of the pharmacology, mechanism of action, substrate specificity, and clinical application. *Pharmacol Rev.* 2012; 64:520-539, incorporated herein by reference in its entirety. However, the catalytic activity of ALDH1a1 that was inhibited by disulfiram and its analogues I-2a-I-2c was completely restored by the addition of dithiothreitol. Given this fact, other molecules, such as cysteamine (3), cystamine (4), and N-acyl-L-cysteine (5) that are known to form disulfide bonds with cysteine, were tested. However, none of them showed any activity against ALDH1a1, nor ALDH2 (see Table I).

ALDH1a1 has a larger substrate tunnel than that of ALDH2. Therefore, the applicant has demonstrated that replacing disulfiram ethyl groups with larger groups is a valid approach for developing selective inhibitors. Notably, the derivative I-2b showed a comparable activity to disulfiram against ALDH1a1. However, it is completely devoid of inhibitory activity against ALDH2.

Example 9

MAGL Enzyme Inhibition Assay

The compounds II-2a to II-2m and controls in Table II were tested in 10-dose $IC_{50}$ mode, with 3-fold serial dilution at a starting concentration of 100 µM for compounds (II-2a-m) and a concentration of 10 µM for JZL184 used as a positive control. The assay buffer (10 mM Tris-HCl with 1 mM EDTA, pH 7.2) was used to dilute the FAAH human recombinant enzyme (Reaction Biology Corp., Malvern, 19355, PA, USA) at a final concentration of 10 nM. The substrate, 4-nitrophenylacetate, was used as a final concentration of 250 µM. The plate was mixed for 30 s and incubated at room temperature for 30 min. The plate was read at an absorption wavelength of 405 nm to detect the release of the by-product 4-nitrophenol. The measurement of $IC_{50}$ for compound II-2d was repeated in presence 10 mM of dithiothreitol to check the reversibility of the MAGL inhibition by our compounds.

Example 10

FAAH Enzyme Inhibition Assay

FAAH inhibition assay was performed using Fatty Acid Amide Hydrolase Inhibitor Screening Assay Kit (Item #10005196), Cayman (1180 E Ellsworth Rd Ann Arbor, MI, USA). The compounds were tested in 10-dose $IC_{50}$ mode, with 3-fold serial dilution at a starting concentration of 100 µM for compounds (II-2a to II-2m) and a concentration of 5 µM for JZL195 used as a positive control. Manufacturer's protocol was followed to perform the assay. The assay buffer (125 mM Tri-HCl with 1 mM EDTA, pH 9.0) was used to dilute the FAAH human recombinant enzyme. AMC-Arachidonoyl amide, at a concentration of 400 µM was then used as the FAAH substrate. Samples were mixed for 30 s and incubated at 37° C. for 30 min. The fluorescent by-product AMC (7-amino-4-methylcoumarin) released by the FAAH enzyme was detected and quantified at an excitation wavelength of 355 nm and emission wavelength of 460 nm.

Example 11

Inhibitory Activities Against MAGL and FAAH

The inhibitory activity of the thiuram disulfides was evaluated in vitro against human MAGL (hMAGL) and human FAAH (hFAAH), as shown in Table II below.

TABLE II*

Inhibition of hMGAL and hFAAH by disulfiram and its analogues II-2b-II-2m**

| Compound. | $R^1$ | $R^2$ | $IC_{50}$ (µM) ± SE (hMAGL) | $IC_{50}$ (µM) ± SE (hFAAH) |
|---|---|---|---|---|
| II-2a (Disulfiram) | Et | Et | 0.95 ± 0.26 | 36.20 ± 10.99 |
| II-2b | —CH(CH$_3$)$_2$ | —CH(CH$_3$)$_2$ | 1.89 ± 0.37 | NI |
| II-2c | —CH$_2$CH$_2$CH$_2$CH$_3$ | —CH$_2$CH$_2$CH$_2$CH$_3$ | 7.14 ± 0.21 | NI |
| II-2d | —CHCH$_2$(CH$_3$)$_2$ | —CHCH$_2$(CH$_3$)$_2$ | 13.42 ± 4.79 | NI |
| II-2e | Et | —CH$_2$CH$_2$OH | 0.72 ± 0.20 | 25.35 ± 3.26 |
| II-2f | Et | —CH$_2$CH$_2$COOH | 0.87 ± 0.21 | 121.76 ± 1.57 |
| II-2g | Et | —CH$_2$CH$_2$COOEt | 3.53 ± 1.32 | 10.05 ± 0.68 |
| II-2h | Et | —CH$_2$—C$_6$H$_5$ | 5.53 ± 2.62 | NI |

TABLE II*-continued

Inhibition of hMGAL and hFAAH by disulfiram and its analogues II-2b-II-2m**

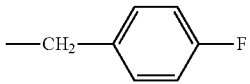

| Compound. | R¹ | R² | IC$_{50}$ (μM) ± SE (hMAGL) | IC$_{50}$ (μM) ± SE (hFAAH) |
|---|---|---|---|---|
| II-2i | Et | —CH$_2$—C$_6$H$_4$—F | 3.58 ± 1.54 | NI |
| II-2j | Et | —CH$_2$—C$_6$H$_4$—OH | 3.71 ± 1.28 | 38.26 ± 7.96 |
| II-2k | Et | —CH$_2$—C$_6$H$_4$—COOH | 22.63 ± 16.83 | NI |
| II-2l | Et | —CH$_2$—C$_6$H$_4$—COOEt | 5.03 ± 2.35 | NI |
| II-2m | —CH$_2$—C$_6$H$_5$ | —CH$_2$—C$_6$H$_5$ | 3.58 ± 0.95 | NI |
| JZl-184 | | | 0.02 ± 0.00 | — |
| JZL-195 | — | | — | 0.04 ± 0.02 |

*JZL-184 and JZL-195 were included in the test as known inhibitors. The data are presented as the average of at least two different experiments + the standard. NI: no inhibition seen at the tested conditions.
**Several compounds in Tables I and II are denoted using two naming conventions. Specifically, compounds II-2b, II-2c, II-2d, II-2e, II-2f, II-2h, II-2i, II-2j, II-2k, and II-2m in Table II correspond to compounds I-2h, I-2i, I-2j, I-2f, I-2e, I-2a, I-2b, I-2c, I-2d, and I-2k in Table I, respectively.

Disulfiram is a potent irreversible inhibitor of MAGL, and it showed an IC$_{50}$ in the micromolar range, in agreement with the values reported in the literature. See Kapanda, C. N.; Muccioli, G. G.; LaBar, G.; Poupaert, J. H.; Lambert, D. M. Bis(dialkylaminethiocarbonyl)disulfides as Potent and Selective Monoglyceride Lipase Inhibitors. *J. Med. Chem.* 2009, 52, 7310-7314, incorporated herein by reference in its entirety. In order to elucidate the structure-activity relationship of disulfiram derivatives, the N-ethyl groups of disulfiram were replaced so as to modify the bulkiness, hydrophobicity and hydrophilicity, as discussed below. Replacing the ethyl groups with an isopropyl motif (II-2b) had no significant effect on the activity. However, the introduction of a much bulkier alkyl group, such as butyl (II-2c) or isobutyl (II-2d), decreased the inhibitory activity by up to 15-fold, introducing polar functional groups like hydroxyl (II-2e) or carboxylate (II-2f) onto the two ethyl groups of disulfiram also seemed to be beneficial for the anti-MAGL activity. The diester derivative of the latter (II-2g), which may serve as a CNS-penetrating prodrug, also showed an MAGL-inhibitory activity in the low micromolar range. Furthermore, replacing two of the four ethyl groups in disulfiram with benzyl motifs was generally well tolerated, as compound (II-2h) retained the inhibitory activity of the reference compound, disulfiram. Substituting the phenyl para position of (II-2h) with a small electronegative group, such as a fluoride (II-2i) or a hydroxyl (II-2j) group, had practically no effect on the inhibitory activity, whereas introducing a carboxylate functional group at the same position of (II-2k) caused a 20-fold decrease in the activity against MAGL. The esterification of the carboxylate functions of the latter compound restored the activity to that of the non-substituted derivative (II-2h). No significant change in activity was noted following the replacement of all four ethyl groups of disulfiram with benzyl groups (II-2m).

Example 12

Mechanistic Studies

The applicant investigated whether the inhibition of the MAGL manifested by the developed derivatives was irreversible and whether it was caused by the carbamylation of Cys208 and/or Cys242 located close to the catalytic Ser132. See Kapanda, C. N.; Muccioli, G. G.; LaBar, G.; Poupaert, J. H.; Lambert, D. M. Bis(dialkylaminethiocarbonyl)disulfides as Potent and Selective Monoglyceride Lipase Inhibitors. *J. Med. Chem.* 2009, 52, 7310-7314; and Saario, S. M.; Salo-Ahen, O. M. H.; Nevalainen, T.; Poso, A.; Laitinen, J. T.; Jarvinen, T.; Niemi, R. Characterization of the Sulfhydryl-Sensitive Site in the Enzyme Responsible for Hydrolysis of 2-Arachidonoyl-Glycerol in Rat Cerebellar Membranes. *Chem. Biol.* 2005, 12, 649-656, each incorporated herein by reference in their entirety. This was achieved by testing the inhibitory activity of compound (II-2d) in the absence and presence dithiothreitol (10 mM). The hydrolytic activity of MAGL inhibited by (II-2d) was restored upon the addition of dithiothreitol, thereby confirming that the developed compounds inhibit MAGL via a similar mechanism to that of disulfiram.

The selectivity of the developed molecules was assessed by evaluating their in vitro inhibitory activity against FAAH. Under the assay conditions described below, disulfiram showed an inhibitory activity against FAAH attested by an $IC_{50}$ of 36 μM, which is ten times less than that reported in the literature. See Kapanda, C. N.; Muccioli, G. G.; LaBar, G.; Poupaert, J. H.; Lambert, D. M. Bis(dialkylaminethiocarbonyl)disulfides as Potent and Selective Monoglyceride Lipase Inhibitors. *J. Med. Chem.* 2009, 52, 7310-7314, incorporated herein by reference in its entirety. Interestingly, disulfiram analogues with bulkier alkyl groups (II-2c, II-2d) showed no inhibition of FAAH. By contrast, the introduction of polar functional groups on the two ethyl groups of disulfiram (II-2e-g) restored the FAAH inhibitory activity at the low micromolar range. With the exception of the phenolic derivatives (II-2j), replacing the two ethyl groups in disulfiram with substituted or nonsubstituted benzyl motifs yielded compounds that were devoid of anti-FAAH activity (II-2h,i and II-2k,l). Replacing all four ethyl groups of disulfiram with benzyl groups (II-2m) also led to the complete loss of FAAH inhibitory activity.

Example 13

Additional Disulfiram Derivatives

Additional disulfiram derivatives and their effects against ALDH1a1 and ALDH2 are summarized in Table III below.

TABLE III

| # | $R^1$ | $R^2$ | Aldh1a1 ($IC_{50}$, μM) ± SE | Aldh2 ($IC_{50}$, μM) ± SE |
|---|---|---|---|---|
| III-2i | Et | 4-methylbenzyl | No inhibition | No inhibition |
| III-2j | Et | 4-chlorobenzyl | 0.86 ± 0.68 | No inhibition |
| III-2k | Et | 2-fluorobenzyl | 0.59 ± 0.46 | No inhibition |
| III-2l | Et | 3-fluorobenzyl | 0.31 ± 0.14 | No inhibition |

TABLE III-continued

| # | $R^1$ | $R^2$ | Aldh1a1 ($IC_{50}$, μM) ± SE | Aldh2 ($IC_{50}$, μM) ± SE |
|---|---|---|---|---|
| III-2m | Et | 4-methoxybenzyl | 0.58 ± 0.41 | No inhibition |
| III-1n | Et | 4-trifluoromethylbenzyl | No inhibition | No inhibition |
| III-2o | Et | 4-pyridylmethyl | 5.76 ± 4.01 | No inhibition |
| III-2p | Et | 2-furylmethyl | 0.39 ± 0.27 | 200.22 ± 129.08 |
| III-2q | Et | 2-thienylmethyl | 0.39 ± 0.31 | No inhibition |
| III-2r | Et | 3-thienylmethyl | 0.17 ± 0.10 | No inhibition |

The compounds in Table III were prepared according to Method I described in Example 1. Specifically, $CS_2$ (2.0 mmol) was added to a solution of appropriate amine (4 mmol) in DMF (4 mL) in an ice-water bath and the mixture was stirred for 5 min. $CBr_4$ (2 mmol) was added and the mixture was stirred at r.t. for 30 min. The mixture was poured into ice-water (40 mL) with stirring, then extracted with $CH_2Cl_2$ (40 mL then 20 mL). The combined organic layers were dried ($MgSO_4$) and concentrated. In order to remove the DMF, 10 mL of toluene was added to the residue and evaporated under high vacuum. This step was repeated 3 times. The crude was subjected to column chromatography to give disulfiram derivatives III-2i to III-2r.

Example 14

Characterizations of Additional Disulfiram Derivatives bis (N-4-Methylbenzyethylthiocarbamoyl) disulphide (III-2i):

Column chromatography: Silica Gel, $CHCl_3$, Yield: 34.8%, IR: 2974, 2928, 1603, 1514, 1481, 1408, 1188, 920, 737, 750 cm$^{-1}$, $^1$H NMR (400 MHz, $CDCl_3$): 1.27-1.44 (6H, bs), 2.35 (6H, s), 4.00 (4H, bs), 5.20-5.35 (4H, bs), 7.16-7.32 (8H, m). $^{13}$C NMR (100 MHz, CDCl$_3$): 11.16, 13.24, 21.20, 47.05, 51.94, 55.62, 59.33, 127.48, 127.79, 129.45, 129.66, 131.48, 132.20, 137.55, 137.99, 193.65, 195.10. HR-MS (ESI$^+$) m/z [M+1] calculated 449.1214 found 449.1199.

bis (N-4-Chlorobenzylethylthiocarbamoyl) disulphide (III-2j):

Column chromatography: Silica Gel, CHCl$_3$. Yield: 52.3%. IR: 2976, 2930, 1481, 1402, 1346, 1190, 1090, 922, 789, 750 cm$^{-1}$. $^1$H NMR (400 MHz, CDCl$_3$): 1.27-1.44 (6H, bs), 4.00 (4H, bs), 5.18-5.32 (4H, bs), 7.26-7.37 (8H, m). $^{13}$C NMR (100 MHz, CDCl$_3$): 11.27, 13.38, 47.53, 52.27, 55.1, 58.99, 129.04, 129.09, 129.28, 133.08, 133.75, 134.24, 193.72, 195.52. HR-MS (ESI$^+$) m/z [M+1] calculated 489.0121 found 489.0128.

bis (N-2-Fluorobenzylethylthiocarbamoyl) disulphide (III-2k):

Column chromatography: Silica Gel, CHCl$_3$. Yield: 17.7%. IR: 2976, 2932, 1479, 1454, 1414, 1352, 1227, 1096,922, 750 cm$^{-1}$. $^1$H NMR (400 MHz, CDCl$_3$): 1.29-1.47 (6H, bs), 4.04 (4H, bs), 5.28-5.41 (4H, bs), 7.09-7.52 (8H, m). $^{13}$C NMR (100 MHz, CDCl$_3$): 11.25, 13.37, 47.79, 49.22, 52.45, 52.91, 115.32, 115.53, 121.78, 122.19, 124.72, 129.56, 159.57, 162.02, 194.12, 195.49. HR-MS (ESI$^+$) m/z [M+1] calculated 457.0712 found 457.0707.

bis (N-3-Fluorobenzylethylthiocarbamoyl) disulphide (III-2l):

Column chromatography: Silica Gel, CHCl$_3$. Yield: 57.4%, IR: 2978, 2932, 1614, 1589, 1481, 1439, 1412, 1346, 1250, 941, 777, 746, 681 cm$^{-1}$. $^1$H NMR (400 MHz, CDCl$_3$): 1.28-1.46 (6H, bs), 4.02 (4H, bs), 5.22-5.35 (4H, bs), 6.99-7.35 (8H, m). $^{13}$C NMR (100 MHz, CDCl$_3$): 11.24, 13.35, 47.56, 52.35, 55.25, 59.08, 114.64, 115.11, 122.24, 130.47, 130.70, 137.21, 137.76, 161.91, 164.36, 193.81, 195.62. HR-MS (ESI$^+$) m/z [M+1] calculated 457.0712 found 457.0709.

bis (N-4-Methoxybenzylethylthiocarbamoyl) disulphide (III-2m):

Column chromatography: Silica Gel, CHCl$_3$. Yield: 12.8%. IR: 2930, 2833, 1611, 1510, 1481, 1412, 1244, 1175, 1107, 1030, 916, 789, 515 cm$^{-1}$. $^1$H NMR (400 MHz, CDCl$_3$): 1.25-1.42 (6H, bs), 3.79 (6H, s), 3.99 (4H, bs), 5.16-5.31 (4H, bs), 6.86-7.38 (8H, m). $^{13}$C NMR (100 MHz, CDCl$_3$): 11.18, 13.28, 46.96, 51.80, 55.38 (2C), 59.10, 114.19, 114.40, 126.48, 127.38, 129.08, 129.30, 159.36, 159.59, 193.44, 195.10. HR-MS (ESI$^+$) m/z [M+1] calculated 481.1112 found 481.1102.

bis (N-4-trifluoromethylbenzylethylthiocarbamoyl) disulphide (III-2n):

Column chromatography: Silica Gel, CHCl$_3$. Yield: 17.4%. IR: 2980, 2934, 1618, 1483, 1410, 1321, 1107, 1016, 928, 752, 650 cm$^{-1}$. $^1$H NMR (400 MHz, CDCl$_3$): 1.30-1.47 (6H, bs), 4.04 (4H, q), 5.28-5.41 (4H, bs), 7.42-7.65 (8H, m). $^{13}$C NMR (100 MHz, CDCl$_3$): 11.28, 13.44, 47.94, 52.56, 55.23, 59.22, 122.76, 125.47, 125.87, 126.09, 127.75, 128.17, 129.96, 130.28, 138.71, 139.22, 193.89, 195.79. HR-MS (ESI$^+$) m/z [M+1] calculated 557.0648 found 557.0676.

bis (N-(4-pyridylmethyl) ethylthiocarbamoyl) disulphide (III-2o):

Column chromatography: Silica Gel, CHCl$_3$-MeOH (98-2). Yield: 9.1%. IR: 2974, 2928, 1597, 1562, 1481, 1410, 1248, 1190, 930, 783, 629, 471 cm$^{-1}$. $^1$H NMR (400 MHz, CDCl$_3$): 1.21-1.43 (6H, bs), 2.51 (0.4H, bs), 3.99-4.04 (3.6H, q), 5.18-5.29 (4H, bs), 7.15-7.28 (4H, m), 8.51-8.58 (4H, m). $^{13}$C NMR (100 MHz, CDCl$_3$): 11.19 (CH$_3$), 13.37, 48.21, 52.79, 54.49, 58.55, 121.89, 122.00, 143.74, 144.05, 149.75, 150.09, 193.86, 195.61. HR-MS (ESI$^+$) m/z [M+1] calculated 423.0806 found 423.0813.

bis (N-(2-furylmethyl) ethylthiocarbamoyl) disulphide (III-2p):

Column chromatography: Silica Gel, CHCl$_3$. Yield: 48.2%. IR: 3113, 2976, 2932, 1479, 1412, 1344, 1260, 1182, 1146, 1011, 935, 733, 598 cm$^{-1}$. $^1$H NMR (400 MHz, CDCl$_3$): 1.22-1.40 (6H, bs), 4.07 (4H, bs), 5.20-5.26 (4H, bs), 6.34-6.51 (4H, m), 7.38 (2H, m). $^{13}$C NMR (100 MHz, CDCl$_3$): 11.05, 13.19, 47.70, 49.05, 52.45, 52.61, 110.12, 110.78, 142.51, 142.97, 148.25, 148.85, 194.02, 194.44. HR-MS (ESI$^+$) m/z [M+1] calculated 401.0486 found 401.0474.

bis (N-(2-thienylmethyl) ethylthiocarbamoyl) disulphide (III-2q):

Column chromatography: Silica Gel, CHCl$_3$. Yield: 14.2%. IR: 3069, 2980, 2928, 1531, 1483, 1412, 1341, 1260, 1155, 991, 924, 795, 725, 706, 640, 511 cm$^{-1}$. $^1$H NMR (400 MHz, CDCl$_3$): 1.29-1.46 (6H, bs), 4.03 (4H, bs), 5.43 (4H, bs), 6.97-7.26 (6H, m). $^{13}$C NMR (100 MHz, CDCl$_3$): 11.25, 13.33, 47.09, 50.84, 51.90, 54.61, 126.32, 126.44, 127.25, 127.73, 136.99, 137.45, 193.53, 194.45. HR-MS (ESI$^+$) m/z [M+1] calculated 433.0029 found 433.0027.

bis (N-(3-thienylmethyl) ethylthiocarbamoyl) disulphide (III-2r):

Column chromatography: Silica Gel, CHCl$_3$. Yield: 12.0%. IR: 3086, 2974, 2928, 2870, 1533, 1479, 1410, 1344, 1246, 1188, 1105, 1072, 997, 974, 935, 914, 768, 704, 637, 567 cm$^{-1}$. $^1$H NMR (400 MHz, CDCl$_3$): 1.26-1.43 (6H, bs), 4.02 (4H, bs), 5.19-5.32 (4H, bs), 7.13-7.37 (6H, m). $^{13}$C NMR (100 MHz, CDCl$_3$): 11.24 (CH$_3$), 13.34, 47.31, 51.57, 52.11, 55.34, 123.44, 123.76, 126.47, 127.07, 127.25, 127.59, 127.72, 135.36, 135.90, 193.27, 194.76. HR-MS (ESI$^+$) m/z [M+1] calculated 433.0029 found 433.0048.

The invention claimed is:

1. A disulfiram derivative of formula (I),

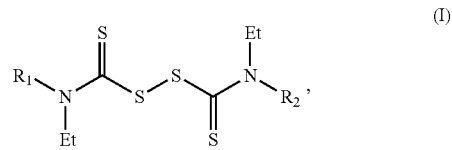

or a salt thereof, a solvate thereof, a tautomer thereof, a stereoisomer thereof, or a mixture thereof, wherein $R_1$ and $R_2$ are each independently,

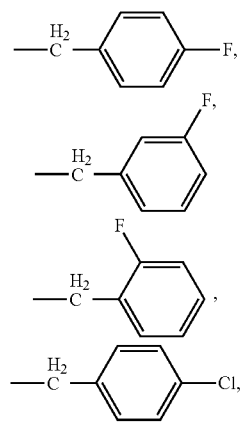

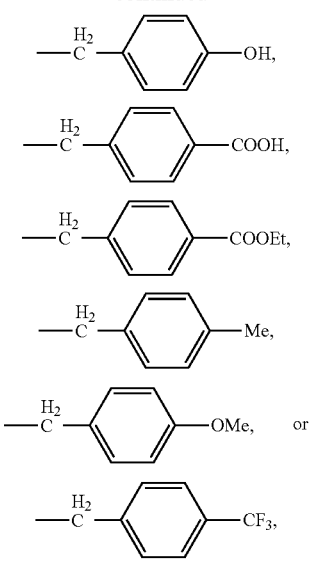

wherein the disulfiram derivative has an IC$_{50}$ for aldehyde dehydrogenase 1a1 (ALDH1a1) in a range of from 0.1 to 25 µM.

2. The disulfiram derivative of claim 1, wherein R$_1$ and R$_2$ are the same.

3. The disulfiram derivative of claim 1, which is

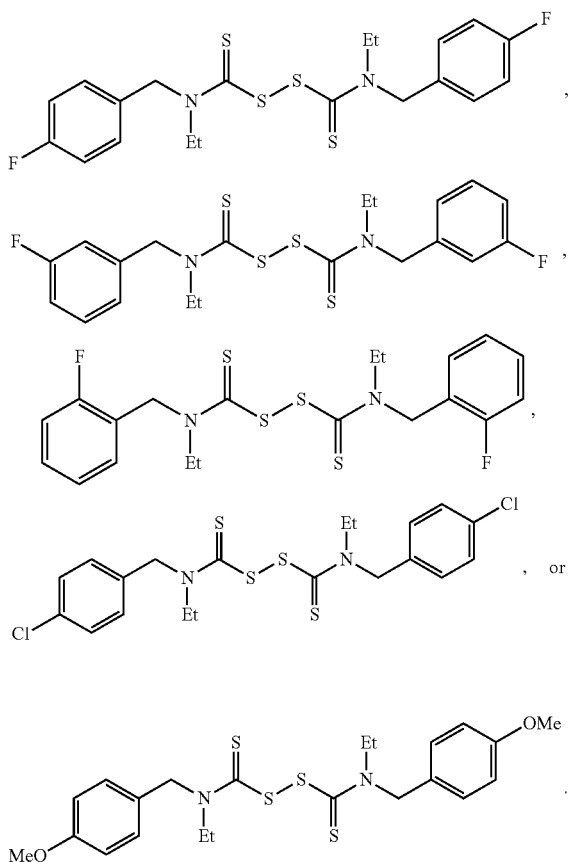

4. The disulfiram derivative of claim 1, which is

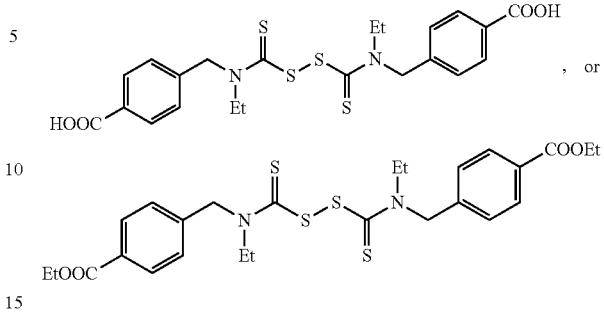

5. The disulfiram derivative of claim 1, which is

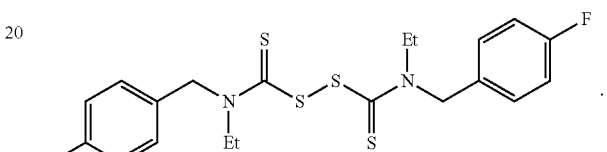

6. The disulfiram derivative of claim 1, which has an IC$_{50}$ for aldehyde dehydrrogenase 1a1 (ALDH1a1) 0.1 to 5 µM.

7. The disulfiram derivative of claim 3, which is devoid of inhibitory activity on aldehyde dehydrogenase 2 (ALDH2).

8. The disulfiram derivative of claim 1, which has an IC$_{50}$ for monoacylglycerol lipase (MAGL) in a range of from 0.5 to 50 µM.

9. The disulfiram derivative of claim 4, which is devoid of inhibitory activity on fatty acid amide hydrolase (FAAH).

10. A pharmaceutical composition, comprising:
the disulfiram derivative of claim 1; and
a pharmaceutically acceptable carrier and/or excipient.

11. The composition of claim 10, comprising the disulfiram derivative of formula (I) in a concentration of 1 to 50 µM, relative to a total volume of the pharmaceutical composition.

12. The composition of claim 10, wherein the pharmaceutically acceptable carrier and/or excipient comprises at least one selected from the group consisting of a buffer, an inorganic salt, a fatty acid, a vegetable oil, a synthetic fatty ester, a surfactant, and a polymer.

13. A disulfiram derivative of structure

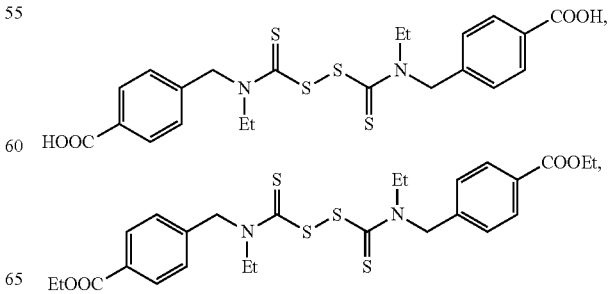

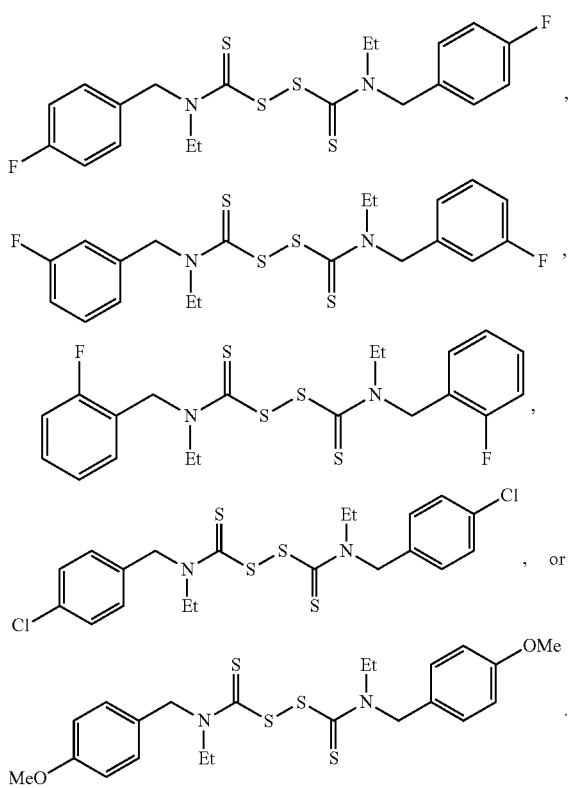
14. The disulfiram derivative of claim 13, which is
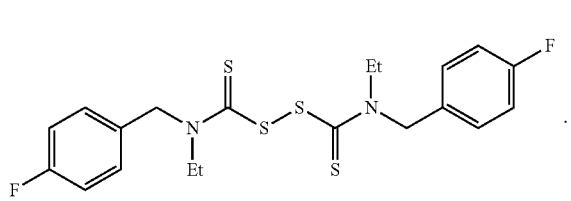 [SMILES: CCN(Cc1ccc(F)cc1)C(=S)SSC(=S)N(CC)Cc1ccc(F)cc1]
15. The disulfiram derivative of claim 13, which is
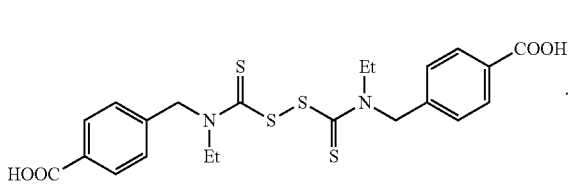 [SMILES: CCN(Cc1ccc(C(=O)O)cc1)C(=S)SSC(=S)N(CC)Cc1ccc(C(=O)O)cc1]
16. The disulfiram derivative of claim 13, which is
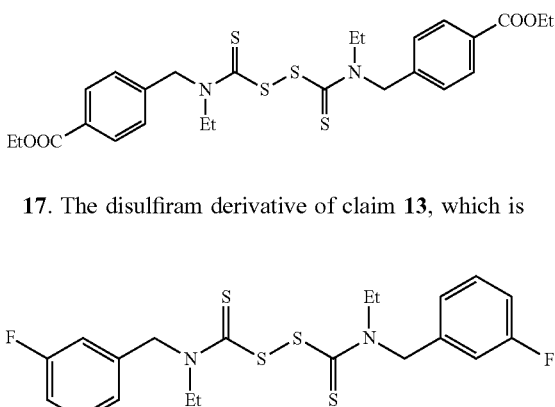
17. The disulfiram derivative of claim 13, which is
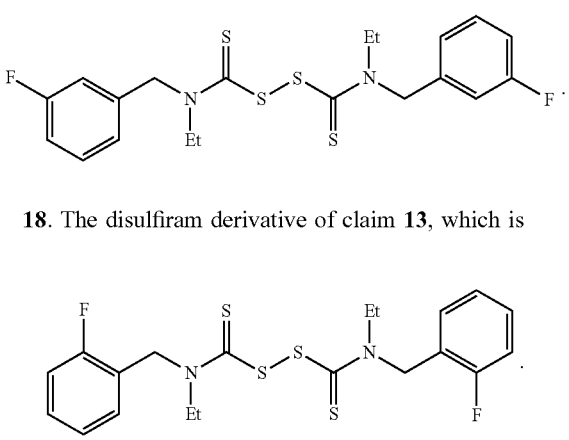
18. The disulfiram derivative of claim 13, which is
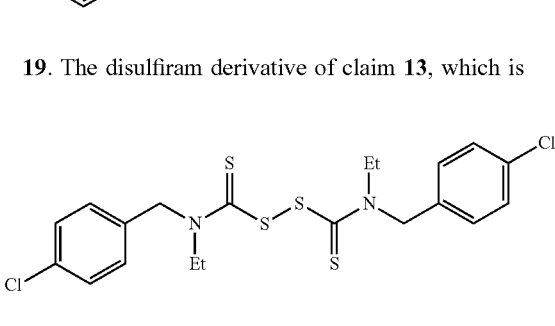
19. The disulfiram derivative of claim 13, which is
20. The disulfiram derivative of claim 13, which is
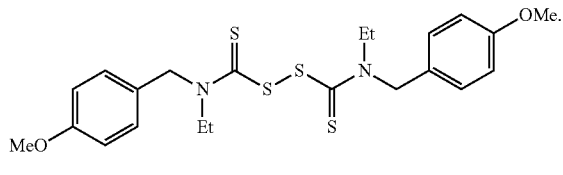 [SMILES: CCN(Cc1ccc(OC)cc1)C(=S)SSC(=S)N(CC)Cc1ccc(OC)cc1]
\* \* \* \* \*